US012797635B2

(12) United States Patent
Chen

(10) Patent No.: US 12,797,635 B2
(45) Date of Patent: Nov. 17, 2026

(54) PHOTOTHERAPY AND PHOTOACOUSTICS

(71) Applicant: Singletto Inc., Seattle, WA (US)

(72) Inventor: James Chongchu Chen, Clyde Hill, WA (US)

(73) Assignee: Singletto Inc., Seattle, WA (US)

( * ) Notice: Subject to any disclaimer, the term of this patent is extended or adjusted under 35 U.S.C. 154(b) by 302 days.

(21) Appl. No.: 18/394,020

(22) Filed: Dec. 22, 2023

(65) Prior Publication Data

US 2025/0073491 A1 Mar. 6, 2025

Related U.S. Application Data

(60) Provisional application No. 63/434,885, filed on Dec. 22, 2022.

(51) Int. Cl.
*A61N 5/06* (2006.01)
*A61N 7/00* (2006.01)

(52) U.S. Cl.
CPC ...... *A61N 5/062* (2013.01); *A61N 2005/0626* (2013.01); *A61N 2005/0658* (2013.01); *A61N 2007/0039* (2013.01)

(58) Field of Classification Search
None
See application file for complete search history.

(56) References Cited

U.S. PATENT DOCUMENTS

| | | | |
|---|---|---|---|
| 2,547,825 | A | 4/1951 | King |
| 2,637,887 | A | 5/1953 | Goodman et al. |
| 3,674,486 | A | 7/1972 | Milgrom |
| 3,817,389 | A | 6/1974 | Weichselbaum |
| 4,059,852 | A | 11/1977 | Crane |
| 4,089,065 | A | 5/1978 | McGee |
| 4,324,005 | A | 4/1982 | Willis |
| 4,382,079 | A | 5/1983 | Marschner |
| 4,395,789 | A | 8/1983 | Bruce |
| 4,402,318 | A | 9/1983 | Swartz |
| 4,685,151 | A | 8/1987 | Kincheloe |
| 4,775,348 | A | 10/1988 | Collins |
| 5,344,051 | A | 9/1994 | Brown |
| 5,366,402 | A | 11/1994 | Rudell et al. |

(Continued)

FOREIGN PATENT DOCUMENTS

| | | | |
|---|---|---|---|
| AU | 2006341380 | B2 | 1/2013 |
| AU | 2013202001 | A1 | 4/2013 |

(Continued)

OTHER PUBLICATIONS

Office Communication for U.S. Appl. No. 18/205,082 mailed Jul. 31, 2025, 17 Pages.

(Continued)

*Primary Examiner* — Yi-Shan Yang

(74) *Attorney, Agent, or Firm* — John W. Branch; Branch Partners PLLC

(57) ABSTRACT

Method and apparatus for directing pulsed light beams at an in vivo treatment site to create thermoelastic expansion of tissue which generates ultrasonic pulse waves in the mega hertz range. One or more photosensitizers are applied to the treatment site. Further, the ultrasonic pulse waves either singly, or in combination with the pulsed light waves cause the activation of the photosensitizers to generate singlet oxygen at the treatment site.

20 Claims, 18 Drawing Sheets

(56) References Cited

U.S. PATENT DOCUMENTS 5,445,608 A 8/1995 Chen et al.
5,526,957 A 6/1996 Brown et al.
5,534,346 A 7/1996 Robinson
5,569,477 A 10/1996 Nesbitt
5,715,837 A 2/1998 Chen
5,741,316 A 4/1998 Chen et al.
5,766,234 A 6/1998 Chen et al.
5,782,896 A 7/1998 Chen et al.
5,814,008 A 9/1998 Chen et al.
5,827,186 A 10/1998 Chen et al.
5,830,526 A 11/1998 Wilson et al.
5,865,840 A 2/1999 Chen
5,891,062 A 4/1999 Schock et al.
5,997,569 A 12/1999 Chen et al.
6,004,510 A 12/1999 Gilbert et al.
6,080,160 A 6/2000 Chen et al.
6,096,066 A 8/2000 Chen et al.
6,210,425 B1 4/2001 Chen
6,238,426 B1 5/2001 Chen
6,273,904 B1 8/2001 Chen et al.
6,281,611 B1 8/2001 Chen et al.
6,317,691 B1 11/2001 Narayan et al.
6,319,273 B1 11/2001 Chen et al.
6,331,744 B1 12/2001 Chen et al.
6,344,050 B1 2/2002 Chen
6,351,854 B1 3/2002 Whalen et al.
6,416,531 B2 7/2002 Chen
6,420,455 B1 7/2002 Landgrebe et al.
6,443,978 B1 9/2002 Zharov
6,454,789 B1 9/2002 Chen et al.
6,520,669 B1 2/2003 Chen et al.
6,572,839 B2 6/2003 Sugita et al.
6,580,228 B1 6/2003 Chen et al.
6,606,767 B2 8/2003 Wong
6,635,267 B1 10/2003 Miyoshi et al.
6,691,898 B2 2/2004 Hurray
6,692,694 B1 2/2004 Curry et al.
6,846,305 B2 1/2005 Smith et al.
6,860,782 B2 3/2005 Hornsby et al.
7,018,395 B2 3/2006 Chen
7,087,219 B2 8/2006 Burzynski et al.
7,211,056 B2 5/2007 Petelenz et al.
7,288,106 B2 10/2007 Heacock et al.
7,320,158 B2 1/2008 Deto et al.
7,320,786 B2 1/2008 Chen
7,511,031 B2 3/2009 Chen
7,611,033 B2 11/2009 Ganzeboom
7,774,867 B2 8/2010 Orita et al.
7,802,572 B2 9/2010 Hahne
RE42,610 E 8/2011 Schramm
8,057,464 B2 11/2011 Chen et al.
8,226,946 B2 7/2012 Chen
8,283,135 B2 10/2012 Doyle et al.
8,293,802 B2 10/2012 Modak et al.
8,365,316 B2 2/2013 Jan et al.
8,402,568 B2 3/2013 Alstin et al.
8,439,674 B2 5/2013 Li et al.
8,450,359 B2 5/2013 McCoy et al.
8,484,809 B2 7/2013 Fiedler
8,545,120 B2 10/2013 Breidenbach et al.
8,616,414 B2 12/2013 Ciavarniia
8,685,005 B2 4/2014 Dahm et al.
8,685,071 B2 4/2014 Burwell et al.
8,759,092 B2 6/2014 Goodrich
8,956,379 B2 2/2015 Luciano et al.
9,073,066 B2 7/2015 Banks et al.
9,080,976 B2 7/2015 Hackbarth et al.
9,114,971 B2 8/2015 Rasmussen et al.
9,140,030 B2 9/2015 Jin
9,149,651 B2 10/2015 Keltner et al.
9,167,880 B2 10/2015 Wilson et al.
9,278,148 B2 3/2016 Fewkes et al.
9,352,074 B2 5/2016 Gros
9,480,760 B2 11/2016 Appeaning et al.
9,527,918 B2 12/2016 Fiori et al.
9,662,258 B2 5/2017 Slattery, Jr. et al.
9,775,389 B2 10/2017 Azzolin et al.
9,931,656 B2 4/2018 Gonzalez et al.
10,105,386 B2 10/2018 Vehige et al.
10,175,687 B2 1/2019 Lema et al.
10,307,610 B2 6/2019 Keltner et al.
10,327,444 B2 6/2019 Topchik
10,666,928 B2 5/2020 Liu
10,786,592 B2 9/2020 Keith
11,419,543 B1 * 8/2022 Peyman ................. C07K 16/22
11,458,220 B2 10/2022 Chen et al.
11,925,717 B2 3/2024 Chen et al.
12,359,369 B2 7/2025 Chen
2002/0069777 A1 6/2002 Rossini et al.
2002/0088825 A1 7/2002 Laverdure
2003/0035750 A1 2/2003 Neuberger
2003/0114434 A1 6/2003 Chen et al.
2004/0170526 A1 9/2004 Curry et al.
2006/0223729 A1 10/2006 Hamblin et al.
2007/0038204 A1 2/2007 Chen et al.
2007/0059316 A1 3/2007 Pallenberg et al.
2007/0059791 A1 3/2007 Goodrich
2007/0129776 A1 6/2007 Robins et al.
2007/0133935 A1 6/2007 Fine
2007/0142880 A1 6/2007 Barnard et al.
2007/0286878 A1 12/2007 Harruna
2008/0015189 A1 1/2008 Hamblin et al.
2008/0030010 A1 2/2008 Millet Lopez
2008/0051736 A1 2/2008 Rioux et al.
2008/0107636 A1 5/2008 Goodrich et al.
2008/0172779 A1 7/2008 Ferguson
2008/0243383 A1 10/2008 Lin
2009/0317293 A1 12/2009 Street et al.
2009/0317436 A1 12/2009 Wilson et al.
2010/0129267 A1 5/2010 Akutsu et al.
2010/0174223 A1 7/2010 Sakamoto et al.
2010/0241054 A1 9/2010 Dacey, Jr. et al.
2010/0261798 A1 10/2010 Neuss et al.
2010/0274330 A1 10/2010 Burwell et al.
2010/0305436 A1 12/2010 Chen et al.
2010/0313890 A1 12/2010 Messier
2011/0008372 A1 1/2011 Chen
2011/0009464 A1 1/2011 Chen
2011/0014239 A1 1/2011 Goodrich
2011/0093003 A1 4/2011 Lee
2011/0110818 A1 5/2011 Mowbray-D Arbela et al.
2011/0112059 A1 * 5/2011 Hasan .................. C07D 501/52
540/219
2011/0152219 A1 6/2011 Stagni et al.
2012/0100039 A1 4/2012 Appeaning et al.
2012/0209359 A1 8/2012 Chen et al.
2013/0060172 A1 3/2013 Palazzolo et al.
2013/0251440 A1 9/2013 Young et al.
2013/0289457 A1 10/2013 Young et al.
2014/0052050 A1 2/2014 Courtin
2014/0076404 A1 3/2014 Tan et al.
2014/0303547 A1 10/2014 Loupis et al.
2015/0202608 A1 7/2015 Masaoka et al.
2015/0231287 A1 8/2015 Lin et al.
2015/0313608 A1 11/2015 Baudenbacher et al.
2016/0091399 A1 3/2016 Chen et al.
2016/0193338 A1 7/2016 Loupis et al.
2016/0220728 A1 8/2016 Adams et al.
2016/0270472 A1 9/2016 Allen et al.
2016/0270895 A1 9/2016 Zoll et al.
2016/0310758 A1 10/2016 Friedman et al.
2016/0358485 A1 12/2016 Sommer et al.
2017/0056603 A1 3/2017 Cowan et al.
2017/0202279 A1 7/2017 Mazzarolo et al.
2018/0099063 A1 4/2018 Lyons et al.
2018/0160720 A1 6/2018 Von Hasseln
2018/0214552 A1 8/2018 Sui et al.
2018/0243790 A1 8/2018 Grossman et al.
2018/0369560 A1 12/2018 Ball et al.
2019/0161562 A1 5/2019 Bakar et al.
2019/0192719 A1 6/2019 Drayton et al.
2019/0209857 A1 7/2019 Brawn et al.
2019/0314502 A1 10/2019 Wei et al.
2020/0289985 A1 9/2020 Drake et al.

(56) References Cited

U.S. PATENT DOCUMENTS

| | | | |
|---|---|---|---|
| 2020/0315280 | A1 | 10/2020 | Kaye |
| 2021/0346531 | A1 | 11/2021 | Kim et al. |
| 2022/0054149 | A1 | 2/2022 | Chen et al. |
| 2022/0054667 | A1 | 2/2022 | Chen et al. |
| 2022/0054672 | A1 | 2/2022 | Chen et al. |
| 2022/0061318 | A1 | 3/2022 | Chen et al. |
| 2022/0062460 | A1 | 3/2022 | Wu et al. |
| 2022/0062461 | A1 | 3/2022 | Chen et al. |
| 2022/0096703 | A1 | 3/2022 | Chen et al. |
| 2022/0143243 | A1 | 5/2022 | Chen et al. |
| 2022/0226530 | A1 | 7/2022 | Suetsugu |
| 2023/0035662 | A1 | 2/2023 | Chen et al. |
| 2023/0165988 | A1 | 6/2023 | Chen et al. |
| 2023/0390430 | A1 | 12/2023 | Chen |
| 2024/0052560 | A1 | 2/2024 | Chen |
| 2024/0123108 | A1 | 4/2024 | Chen |
| 2024/0206737 | A1* | 6/2024 | Buchan ................ A61B 5/6898 |
| 2025/0041459 | A1* | 2/2025 | Dai .................... A61K 49/0021 |
| 2025/0082802 | A1 | 3/2025 | Chen et al. |
| 2025/0152987 | A1 | 5/2025 | Chen |

FOREIGN PATENT DOCUMENTS

| | | | |
|---|---|---|---|
| AU | 2015200474 | B2 | 8/2016 |
| AU | 2016235788 | A1 | 9/2016 |
| AU | 2016235771 | B2 | 3/2019 |
| CA | 2276023 | C | 4/2002 |
| CA | 2473924 | A1 | 7/2003 |
| CA | 2537235 | A1 | 1/2005 |
| CA | 2428099 | C | 1/2009 |
| CA | 2733752 | C | 1/2014 |
| CA | 2693491 | C | 10/2014 |
| CN | 102115951 | B | 7/2012 |
| CN | 101479438 | B | 5/2014 |
| CN | 104138310 | A | 11/2014 |
| CN | 104623702 | A | 5/2015 |
| CN | 205094776 | U | 3/2016 |
| CN | 104589717 | B | 3/2017 |
| CN | 208597758 | U | 3/2019 |
| CN | 107353723 | B | 5/2020 |
| CN | 111567937 | A | 8/2020 |
| EP | 1644082 | A2 | 1/2005 |
| EP | 1684865 | A1 | 4/2005 |
| EP | 2181691 | A1 | 5/2010 |
| EP | 1429993 | B1 | 1/2011 |
| EP | 1940907 | B1 | 4/2011 |
| EP | 2428461 | B1 | 4/2013 |
| GB | 2374856 | A | 10/2002 |
| GB | 2482745 | A | 2/2012 |
| JP | 2004-275927 | A | 10/2004 |
| JP | 2004-350935 | A | 12/2004 |
| JP | 2005-009065 | A | 1/2005 |
| JP | 2005-506938 | A | 3/2005 |
| JP | 2005-112791 | A | 4/2005 |
| JP | 4238174 | B2 | 3/2009 |
| JP | 4536377 | B2 | 9/2010 |
| JP | 2014-004329 | A | 1/2014 |
| JP | 5632478 | B2 | 11/2014 |
| JP | 2015-159819 | A | 9/2015 |
| JP | 2018-523517 | A | 8/2018 |
| KR | 2003-48162 | Y1 | 5/2004 |
| KR | 10-0822777 | B1 | 4/2008 |
| KR | 10-2014-0028671 | A | 3/2014 |
| KR | 10-2017-0076342 | A | 7/2017 |
| KR | 10-2017-0082259 | A | 7/2017 |
| KR | 102144502 | B1 | 8/2020 |
| PL | 230175 | B1 | 9/2018 |
| RU | 2397127 | C2 | 8/2010 |
| TW | I610806 | B | 1/2018 |
| WO | 98/32494 | A1 | 7/1998 |
| WO | 99/18924 | A1 | 4/1999 |
| WO | 99/49823 | A1 | 10/1999 |
| WO | 00/04930 | A2 | 2/2000 |
| WO | 00/36983 | A1 | 6/2000 |
| WO | 2004/108249 | A1 | 12/2004 |
| WO | 2005/004704 | A2 | 1/2005 |
| WO | 2005/032459 | A2 | 4/2005 |
| WO | 2005/037372 | A1 | 4/2005 |
| WO | 2006/086770 | A2 | 8/2006 |
| WO | 2007/103781 | A2 | 9/2007 |
| WO | 2008/044222 | A2 | 4/2008 |
| WO | 2008/046019 | A1 | 4/2008 |
| WO | 2009/132223 | A1 | 10/2009 |
| WO | 2010/076658 | A2 | 7/2010 |
| WO | 2010/151563 | A1 | 12/2010 |
| WO | 2014/057116 | A1 | 4/2014 |
| WO | 2014/130740 | A1 | 8/2014 |
| WO | 2016/039812 | A1 | 3/2016 |
| WO | 2016/153910 | A1 | 9/2016 |
| WO | 2018/022926 | A1 | 2/2018 |
| WO | 2018/151236 | A1 | 8/2018 |
| WO | 2019/183320 | A1 | 9/2019 |
| WO | 2021/001441 | A1 | 1/2021 |
| WO | 2021/001445 | A1 | 1/2021 |
| WO | 2022/103775 | A1 | 5/2022 |

OTHER PUBLICATIONS

Piccirillo et al., "Antimicrobial activity of methylene blue and toluidine blue O covalently bound to a modified silicone polymer surface," Journal of Materials Chemistry, 2009, vol. 19, Iss. 34, pp. 6167-6171.

Plotino et al., "Photodynamic therapy in endodontics," International Endodontic Journal, Jun. 2019, vol. 52, Issue 6, pp. 760-774.

Post et al., "Pediatric concussion: biomechanical differences between outcomes of transient and persistent(> 4 weeks) postconcussion symptoms," Journal of Neurosurgery: Pediatrics, Jun. 2017, vol. 19, No. 6, pp. 641-651.

Prausnitz et al., "Microneedle-based vaccines," Vaccines for Pandemic Influenza, Current Topics in Microbiology and Immunology, 2009, vol. 333, pp. 369-393.

Pushalkar et al., "Superhydrophobic Photosensitizers: Airborne 102 Killing of an in Vitro Oral Biofilm at the Plastron Interface," ACS Applied Materials & Interfaces, 2018, vol. 10, No. 30, pp. 25819-25829.

Pyrek, Kelly M., "Portable Medical Equipment: A Significant Source of Transmission," Infection Control Today, https://www.infectioncontroltoday.com/view/portable-medical-equipment-significant-source-transmission/, Accessed: Jul. 2, 2021, pp. 1-9.

Quan et al., "Dose sparing enabled by skin immunization with influenza virus-like particle vaccine using microneedles," Journal of Controlled Release, 2010, vol. 147, Iss. 3, pp. 326-332.

Radiology Info, "Intravascular Ultrasound," https://www.radiologyinfo.org/en/info/ultrasound-intravascular, Accessed: Nov. 22, 2021, pp. 1-6.

Rajesh, S. et al., "Antimicrobial photodynamic therapy: An overview," Journal of Indian Society of Periodontology, 2011, vol. 15, Iss. 4, pp. 323-327.

Russotto, Vincenzo et al., "Bacterial contamination of inanimate surfaces and equipment in the intensive care unit," Journal of Intensive Care, 2015, vol. 3, Article 54, pp. 1-8.

Jerard et al., "Main Properties of the THERAFLEX MB-Plasma System for Pathogen Reduction," Transfusion Medicine and Hemotherapy, 2011, vol. 38, No. 1, pp. 55-64.

Shang et al., "Accelerated In Vitro Degradation of Optically Clear Low 13-Sheet Silk Films by Enzyme-Mediated Pretreatment," Translational Vision Science & Technology, vol. 2, No. 3, Article 2, pp. 1-11.

Sharma et al., "Natural Edible Oils: Comparative Health Aspects of Sesame, Coconut, Mustard (Rape Seed) and Groundnut (Peanut) A Biomedical Approach," Biomedical Journal of Scientific & Technical Research, 2017, vol. 1, Iss. 5, pp. 1375-1377.

Chikara et al., "Near-infrared photothernmal/photodynamic therapy with indocyanine green induces apoptosis of hepatocellular carcinoma cells through oxidative stress," Scientific Reports, vol. 7, Article No. 13958, pp. 1-8.

Sigma-Aldrich, "Hyaluronic acid sodium salt" https//www.sigmaaldrich.com/US/en/procluc1/sigma/h5542, Accessed: Nov. 22, 2021, pp. 1-5.

(56) References Cited

OTHER PUBLICATIONS

Siracusa, Valentina, "Food Packaging Permeability Behaviour: A Report," International Journal of Polymer Science, 2012, vol. 2012, pp. 1-11.
Slobounov, Semyon M. et al., "The effect of repetitive subconcussive collisions on brain integrity in collegiate football players over a single football season: A multi-modal neuroimaging study," NeuroImage: Clinical, 2017, vol. 14, pp. 708-718.
Smartblend, "Cocktail foams, airs and bubbles—How to make them," https://www.smartblend.co.uk/blog/cocktail-foams-airs-and-bubbles-and-how-to-make-them, Accessed: Dec. 6, 2021, pp. 1-16.
Spagnul et al., "Immobilized Photosensitisers for antimicrobial applications," Journal of Photochemistry and Photobiology, 2015, vol. 150, pp. 11-30.
Sunday et al., "A simple, inexpensive method for gas-phase singlet oxygen generation from sensitizer-impregnated filters: Potential application to bacteria/virus inactivation and pollutant degradation," Science of the Total Environment, 2020, vol. 746, Article No. 141186, pp. 1-6.
Tamstech, "Air Permeable (Breathable) Film," http://tamstech.net/airfilm/, Accessed: Jul. 2, 2021, pp. 1-6.
Trempolec et al., "Photodynamic Therapy-Based Dendritic Cell Vaccination Suited to Treat Peritoneal Mesothelioma," Cancers, Feb. 2020, vol. 12, pp. 1-16.
University of Southampton, "New Optical Fiber 3D Printing Technique," Optik & Photonik, 2015, vol. 10, Iss. 4, p. 17.
Ursa BioScience, "Singlet Oxygen Sensitizers," https://ursabioscience.com/technology/singlet-oxygen-sensitizer, Accessed: Mar. 2, 2021, pp. 1-6.
Verma et al., "Visualizing the effectiveness of face masks in obstructing respiratory jets," Physics of Fluids, 2020, vol. 32, pp. 1-7.
Victoria et al., "Viral Nucleic Acids in Live-Attenuated Vaccines: Detection of Minority Variants and an Adventitious Virus," Journal of Virology, 2010, vol. 84, No. 12, pp. 6033-6040.
Waheed et al., "3D printed microfluidic devices: enablers and barriers," The Royal Society of Chemistry, Lab Chip, 2016, vol. 16, Iss. 11, pp. 1-21.
Wakayama et al., "Magnetic Acceleration of Inllaled and Exhaled Flows in Breathing," Japanese Journal of Applied Physics, 2000, vol. 39, pp. L262-L264.
Waldman et al., "Immunization Against influenza Prevention of illness in Man by Aerosoiized Inactivated Vaccine," JAMA, 1969, vol. 207, No. 3, pp. 520-524.
Wang et al., "Choosing optimal wavelength for photodynamic therapy of port wine stains by mathematic simulation," Journal of Biomedical Optics, 2011, vol. 16, No. 9, pp. 1-9.
Weaver, Eric A., "Dose Effects of Recombinant Adenovirus Immunization in Rodents," Vaccines, 2019, vol. 7, No. 4:144, pp. 1-11.
Wojnarowicz et al., "Considerations for Experimental Animal Models of Concussion, Traumatic Brain Injury, and Chronic Traumatic Encephalopathy-These Matters Matter," Frontiers in Neurology, Jun. 2017, vol. 8, Article 240, pp. 1-14.
Wood et al., "Erythrosine is a potential photosensitizer for the photodynamic therapy of oral plaque biofilms," Journal of Antimicrobial Chemotherapy, 2006, vol. 57, Iss. 4, pp. 680-684.
Woolley et al., "Light Penetration and Light-induced Seed Germination in Soil," Plant Physiology, Apr. 1978, vol. 61, No. 4, pp. 597-600.
Wu et al., "A Compact Magnetic Field-Based Obstacle Detection and Avoidance System for Miniature Spherical Robots," Sensors, May 2017, vol. 17, No. 6:1231, pp. 1-20.
Yamada, Shinya, "Cerebrospinal fluid physiology: visualization of cerebrospinal fluid dynamics using the magnetic resonance imaging Time-Spatial Inversion Pulse method," Croatian Medical Journal, Aug. 2014, vol. 55, No. 4, pp. 337-346.
Yang et al., "3D Printing of Polymeric Multi-Layer Micro-Perforated Panels for Tunable Wideband Sound Absorption," Polymers, 2020, vol. 12, No. 360, pp. 1-17.
Jing et al., "Green preparation of carbon dots by Jinhua bergamot for sensitive and selective fluorescent detection of Hg2+ and Fe3+," Sensors and Actuators B: Chemical, 2015, vol. 214, pp. 29-35.
Zhao et al., "Singlet oxygen generation on porous superhydrophobic surfaces: effect of gas flow and sensitizer wetting on trapping efficiency," The Journal of Physical Chemistry A, 2014, vol. 118, No. 45, pp. 10364-10371.
Zhu et al., "In Vivo Measurements of Human Brain Displacement," 2003 Summer Bioengineering Conference, Jun. 2003, pp. 1-2.
International Preliminary Report on Patentability Chapter I for International Patent Application No. PCT/US2021/058678 mailed May 25, 2023, 6 Pages.
International Preliminary Report on Patentability Chapter I for International Patent Application No. PCT/US2021/046722 mailed Mar. 2, 2023, 7 Pages.
International Search Report and Written Opinion for International Patent Application No. PCT/US2021/058678 mailed Jan. 25, 2022, 8 Pages.
International Search Report and Written Opinion for International Patent Application No. PCT/US2021/046416 mailed Nov. 8, 2021, 9 Pages.
International Search Report and Written Opinion for International Patent Application No. PCT/US2021/046417 mailed Nov. 30, 2021, 11 Pages.
International Search Report and Written Opinion for International Patent Application No. PCT/US2021/046419 mailed Feb. 2, 2022, 11 Pages.
International Search Report and Written Opinion for International Patent Application No. PCT/US2021/046722 mailed Dec. 6, 2021, 9 Pages.
International Search Report and Written Opinion for International Patent Application No. PCT/US2021/048444 mailed Feb. 1, 2022, 14 Pages.
Office Communication for U.S. Appl. No. 17/522,811 mailed Jul. 26, 2022, 9 Pages.
Office Communication for U.S. Appl. No. 18/205,082 mailed Aug. 16, 2023, 13 Pages.
Atilgan et al., "Detoxification of a Sulfur Mustard Simulant Using a BODIPY Functionalized Zirconium-Based Metal—Organic Framework", ACS Appl. Mater. Interfaces 2017, vol. 9, pp. 24555-24560.
Atilgan et al., "Detoxification of a Sulfur Mustard Simulant Using a BODIPY Functionalized Zirconium-Based Metal—Organic Framework", Supporting Information, ACS Appl. Mater. Interfaces 2017, vol. 9, pp. S1-S14.
Office Communication for U.S. Appl. No. 18/205,082 mailed Jan. 28, 2025, 16 Pages.
Office Communication for U.S. Appl. No. 18/231,922 mailed Feb. 10, 2025, 12 Pages.
Office Communication for U.S. Appl. No. 18/205,082 mailed Apr. 7, 2025, 4 Pages.
Office Communication for U.S. Appl. No. 18/231,922 mailed Apr. 9, 2025, 4 Pages.
Office Communication for U.S. Appl. No. 18/379,863 mailed Mar. 13, 2025, 11 Pages.
Office Communication for U.S. Appl. No. 18/205,082 mailed May 16, 2024, 15 Pages.
Huang et al., "Chitosan and its derivatives as vehicles for drug delivery," Drug Delivery, 2017, vol. 24, No. 2, pp. 108-113.
Quoc et al., "Optimization of an Accelerometer and Gyroscope-Based Fall Detection Algorithm," Journal of Sensors, Apr. 2015, vol. 2015, Article ID 452078, pp. 1-8.
Hwang et al., "Study of Singlet Oxygen Dynamics on Silicon Polymer Matrix," Journal of Analytical Methods in Chemistry, 2019, vol. 2019, pp. 1-6.
Ismail et al., "Efficacy of a Novel Light-Activated Antimicrobial Coating for Disinfecting Hospital Surfaces," Infection Control and Hospital Epidemiology, 2011, vol. 32, No. 11, pp. 1130-1132.
Ji et al., "In Vivo Measurements of Human Brain Displacement," Stapp Car Crash Journal, Nov. 2004, vol. 48, pp. 1-11.
Jaesung et al., "Photosensitized Production of Singlet Oxygen via C60 Fullerene Covalently Attached to Functionalized Silica-coated

(56) References Cited

OTHER PUBLICATIONS

Stainless-Steel Mesh: Remote Bacterial and Viral Inactivation," Applied Catalysts B: Environmental, 2020, vol. 270, Article No. 118862, pp. 1-9.
Michele et al., "Light Sources and Dosimetry Techniques for Photodynamic Therapy," Photochemistry and Photobiology, 2020, vol. 96, pp. 280-294.
Kim, Sungho, "High-Speed Incoming Infrared Target Detection by Fusion of Spatial and Temporal Detectors," Sensors, Mar. 2015, vol. 15, No. 4, pp. 7267-7293.
Kino et al., "Commentary on the Phototoxicity and Absorption of Vitamin B2 and Its Degradation Product, Lumichrome," Pharmaceutica Analytica Acta, 2015, vol. 6, Iss. 8, pp. 1-3.
Kitchen Theory, "Lecithin & Culinary Foam," https://kitchen-theory.com/culinary-foam/, Accessed: Nov. 15, 2021, pp. 1-4.
Klasse, P.J., "Molecular determinants of the ratio of inert to infectious virus particles," Progress in Molecular Biology and Translational Science, 2015, vol. 129, pp. 285-326.
Klausberger et al., "One-shot vaccination with an insect cell-derived low-dose influenza A H7 virus-like particle preparation protects mice against H7N9 challenge," Vaccine, 2014, vol. 32, Iss. 3, pp. 355-362.
Komaiko et al., "Formation of Food-Grade Nanoemulsions Using Low-Energy Preparation Methods: A Review of Available Methods," Comprehensive Reviews in Food Science and Food Safety, 2016, vol. 15, pp. 331-352.
Koral et al., "Alterations in cerebrospinal fluid flow dynamics and pressure gradient generated by acute and chronic changes in intraabdominal pressure: Early results of MRI measurements performed on volunteers at 3 Tesla," European Society of Radiology, EPOS, 2010, Poster No. C-2474, pp. 1-10.
Kumar et al., "Sensing Molecules with Metal-Organic Framework Functionalized Graphene Transistors," Advanced Materials, 2021, vol. 33, Article No. 2103316, pp. 1-12.
Lee et al., "Aerosol Particle Size Distribution and Genetic Characteristics of Aerosolized Influenza A H1N1 Virus Vaccine Particles," Aerosol and Air Quality Research, 2011, vol. 11, pp. 230-237.
Lee et al., "The photodynamic therapy on *Streptococcus* mutans biofilms using erythrosine and dental halogen curing unit," International Journal of Oral Science, 2012, vol. 4, pp. 196-201.
LFA Tablet Presses, "Tablet Binders," https://www.lfatabletpresses.com/articles/tablet-binders, Accessed: Dec. 6, 2021, pp. 1-8.
Li, Dao et al., "Brain Injury Differences in Frontal Impact Crash Using Different Simulation Strategies," Computational and Mathematical Methods in Medicine, 2015, vol. 2015, Article ID 348947, pp. 1-8.
Ji-Yuan et al., "Blue light induced free radicals from riboflavin on *E. coli* DNA damage," Journal of Photochemistry and Photobiology B: Biology, Feb. 2013, vol. 119, pp. 60-64.
Instructables Living, "Bubble Machine," https://www.instructables.com/Bubble-Machine/, Accessed: Nov. 30, 2021, pp. 1-6.
MacoPharma, "THERAFLEX-MB Plasma," https://www.mhlw.go.jp/shingi/2008/05/dl/s0523-7j.pdf, Accessed: Dec. 1, 2021, pp. 1-33.
Makdoumi et al., "Different photodynamic effects of blue light with and without riboflavin on methicillin-resistant *Staphylococcus aureus* (MRSA) and human keratinocytes in vitro," Lasers in Medical Science, 2019, vol. 34, No. 9, pp. 1799-1805.
Malewar, Amit, "Tengujo, the world's thinnest paper, almost completely transparent," Inceptive Mind, https://www.inceptivemind.com/tengujo-worlds-thinnest-paper-nearly-transparent/13273/, Accessed: Nov. 15, 2021, pp. 1-5.
Marcus et al., "In Vitro Analysis of Virus Particle Subpopulations in Candidate Live-Attenuated Influenza Vaccines Distinguishes Effective from ineffective Vaccines," Journal of Viroiogy, 2010, vol. 84, No. 21, pp. 10974-10981.
Martin, GT, "Acute brain trauma," Annals of the Royal College of Surgeons of England, Jan. 2016, vol. 98, No. 1, pp. 6-10.
Matsui et al., "Real-Time Near-Infrared Fluorescence-Guided Identification of the Ureters using Methylene Blue," Surgery, 2010, vol. 148, No. 1, pp. 78-86.
Maves et al., "Immunogenicity of a Psoralen-Inactivated Dengue Virus Type 1 Vaccine Candidate in Mice," Clinical and Vaccine Immunology, 2010, vol. 17, No. 2, pp. 304-306.
Meller et al., "Photodisinfection Therapy: Essential Technology for Infection Control," The Infection Prevention Strategy, Jan. 2020, https://infectioncontrol.tips/2020/01/17/photodisinfection-therapy/, Accessed: Jun. 7, 2022, pp. 1-13.
Federica et al., "In vitro photo-induced cytotoxic activity of Citrus bergamia and *C medica* L. cv. Diamante peel essential oils and identified active coumarins," Pharmaceutical Biology, vol. 48, No. 9, pp. 1059-1065.
Mertes et al., "Methylene blue-treated plasma: An increased allergy risk?," The Journal of Allergy and Clinical Immunology, Letters to the Editor, 2012, vol. 130, Iss. 3, pp. 808-812.
Mesquita et al., "Revisiting Current Photoactive Materials for Antimicrobial Photodynamic Therapy," Molecules, 2018, vol. 23, No. 2424, pp. 1-47.
Gabriele et al., "Environmental Contaminants in Hospital Settings and Progress in Disinfecting Techniques," BioMed Research International, 2013, vol. 2013, pp. 1-8.
Meurice et al., "Immunogenicity and Safety of a Live Attenuated Varicella Vaccine (Oka/SB Bio) in Healthy Children," The Journal of Infectious Diseases, 1996, vol. 174, Supplement 3, pp. S324-S329.
Meyer et al., "Aerosolized Ebola vaccine protects primates and elicits lung-resident T cell responses," The Journal of Clinical Investigation, 2015, vol. 125, No. 8, pp. 3241-3255.
Midden et al., "Singlet Oxygen Generation for Solution Kinetics: Clean and Simple," Journal of the American Chemical Society, Jun. 1983, vol. 105, No. 13, pp. 4129-4135.
Mills et al., "Ultraviolet germicidal irradiation of influenza-contaminated N95 filtering facepiece respirators," American Journal of Infection Control, 2018, vol. 46, Iss. 7, pp. e49-e55.
Molitch-Hou, Michael, "First 3D Printed Fiber Optics Created by University of Sydney Researchers with Desktop 3D Printer," 3D Printing Industry, https://3dprintingindustry.com/news/first-3d-printed-fiber-optics-createdby-university-of-sydney-researchers-with-desktop-3d-printer-55047/, 2015, Accessed: Jun. 30, 2021, p. 1.
Moller-Breitkreutz et al., "Inactivation of viruses by chemically and photochemically generated singlet molecular oxygen," Journal of Photochemistry & Photobiology B: Biology, 1995, vol. 30, Iss. 1, pp. 63-70.
Monath et al., "A live, attenuated recombinant West Nile virus vaccine," Proceedings of the National Academy of Sciences, 2006, vol. 103, No. 17, pp. 6694-6699.
Moses, Allistair et al., "Radar-Based Detection and Identification for Miniature Air Vehicles," IEEE International Conference on Control Applications (CCA), Sep. 2011, pp. 933-940.
Myer et al., "Analysis of head impact exposure and brain microstructure response in a season-long application of a jugular vein compression collar: a prospective, neuroimaging investigation in American football," British Journal of Sports Medicine, Oct. 2016, vol. 50, No. 20, pp. 1-11.
Naito et al., "Single-molecule detection of airborne singlet oxygen," Journal of the American Chemical Society, 2006, vol. 128, No. 51, pp. 16430-16431.
Nakonechny et al., "Aspects of Photodynamic Inactivation of Bacteria," Microorganisms, 2020, Chapter 7, pp. 131-151.
Navarro et al., "A Machine Learning Approach to Pedestrian Detection for Autonomous Vehicles Using High-Definition 3D Range Data," Sensors, 2017, vol. 17, No. 1:18, pp. 1-20.
Ng et al., "A Mechanistic End-to-End Concussion Model That Translates Head Kinematics to Neurologic Injury," Frontiers in Neurology, Jun. 2017, vol. 8, Article 269, pp. 1-18.
Noimark et al., "Incorporation of methylene blue and nanogold into polyvinyl chloride catheters; A new approach for light-activated disinfection of surfaces," Journal of Materials Chemistry, 2012, vol. 22, Iss. 30, pp. 15388-15396.
Noimark et al., "Light-activated antimicrobial surfaces with enhanced efficacy induced by a dark-activated mechanism," Chemical science, 2014, vol. 5, pp. 2216-2223.

(56) References Cited

OTHER PUBLICATIONS

Ogilby, Peter R., "Singlet oxygen: There is indeed something new under the sun," Chemical Society Reviews, 2010, vol. 39, No. 8, pp. 3181-3209.
Omnexus: The material selection platform, "Clear Polypropylene (PP) for Transparent Polymer Applications," https://omnexus.specialchem.com/centers/clear-polypropylene/, Accessed: Jul. 1, 2021, p. 1.
Office Communication for U.S. Appl. No. 18/379,863 mailed Sep. 23, 2025, 15 Pages.
Office Communication for U.S. Appl. No. 18/205,082 mailed Apr. 22, 2025, 17 Pages.
Office Communication for U.S. Appl. No. 18/231,922 mailed May 9, 2025, 9 Pages.
Office Communication for U.S. Appl. No. 18/379,863 mailed Oct. 9, 2024, 12 Pages.
Kim et al., "Photocatalytic detoxification of a sulfur mustard simulant under realistic conditions by imidazoline-based porous organic polymer composites", Cell Reports Physical Science, vol. 3, Issue 5, 100888, May 18, 2022, pp. 1-19.
Ayoub et al., "Air oxidation of sulfur mustard gas simulants using a pyrene-based metal—organic framework photocatalyst", Beilstein Journal of Nanotechnology, vol. 10, 2019, pp. 2422-2427.
Ayoub et al., "Air oxidation of sulfur mustard gas simulants using a pyrene-based metal—organic framework photocatalyst", Supporting Information, Beilstein Journal of Nanotechnology, vol. 10, 2019, pp. S1-S10.
Office Communication for U.S. Appl. No. 18/379,863 mailed Jan. 30, 2024, 13 Pages.
Office Communication for U.S. Appl. No. 18/231,922 mailed Mar. 28, 2024, 12 Pages.
"What is Photodisinfection?," Ondine Biomedical Inc, https://ondinebio.com/technology/, Accessed: Jun. 7, 2022, pp. 1-4.
Adepu et al., "Controlled Drug Delivery Systems: Current Status and Future Directions," Molecules, Sep. 2021, vol. 26, No. 19, Article No. 5905, pp. 1-45.
Aebisher et al., "Superhydrophobic Surfaces as a Source of Airborne Singlet Oxygen through Free Space for Photodynamic Therapy," ACS Applied Bio Materials, 2020, vol. 3, No. 4, pp. 2370-2377.
Akasov et al., "Photodynamic therapy of melanoma by blue-light photoactivation of flavin mononucleotide," Scientific Reports, 2019, vol. 9, Article No. 9679, pp. 1-11.
Alander et al., "A Review of Indocyanine Green Fluorescent Imaging in Surgery," international Journal of Biomedical imaging, 2012, vol. 2012, pp. 1-26.
Almeida et al., "Phage Therapy and Photodynamic Therapy: Low Environmental Impact Approaches to Inactivate Microorganisms in Fish Farming Plants," Marine Drugs, 2009, vol. 7, No. 3, pp. 268-313.
Alven et al., "Hyaluronic Acid-Based Scaffolds as Potential Bioactive Wound Dressings," Polymers, 2021, vol. 13, No. 2102, pp. 1-20.
Babbs, Charles F., "Brain motion and deformation during closed head injury in the presence of cerebrospinal fluid," Weldon School of Biomedical Engineering Faculty Publications, Jun. 2004, Paper 41, pp. 1-39.
Gladimir et al., "On the Light Penetration in Natural Sands," 2019 IEEE International Geoscience and Remote Sensing Symposium (IGARSS 2019), 2019, pp. 6933-6936.
Barrett et al., "Vero cell technology for rapid development of inactivated whole virus vaccines for emerging viral diseases," Expert Review of Vaccines, 2017, vol. 16, Iss. 9, pp. 883-894.
Dorota et al., "Bacterial Inactivation by a Singlet Oxygen Bubbler: Identifying Factors Controlling the Toxicity of 102 Bubbles," Environmental Science & Technology, 2012, vol. 46, No. 21, pp. 12098-12104.
Bayly et al., "Deformation of the human brain induced by mild acceleration," Journal of Neurotrauma, NIH Public Access, Author Manuscript, 2005, PMCID PMC2377024, pp. 1-18.
Bazaz et al., "3D Printing of Inertial Microfluidic Devices," Scientific Reports, 2020, vol. 10, Article No. 5929, pp. 1-14.
Bhat et al., "Effectiveness of erythrosine-mediated photodynamic antimicrobial chemotherapy on dental plaque aerobic microorganisms: A randomized controlled trial," Journal of Indian Society of Periodontology, 2017, vol. 21, Iss. 3, pp. 210-215.
Bonetta et al., "Photocatalytic bacterial inactivation by TiO2-coated surfaces," AMB Express, 2013, vol. 3, Article 59, pp. 1-8.
Borkar et al., "Techniques Employed in Production of Traditional Vaccines Commonly Used by Military Forces: A Review," Journal of Archives in Military Medicine, 2019, vol. 7, No. 1-2, pp. 1-12.
Boyce, John M., "Modern technologies for improving cleaning and disinfection of environmental surfaces in hospitals," Antimicrobial Resistance and Infection Control, 2016, vol. 5, Article 10, pp. 1-10.
Buettner et al., "Hydrogen Peroxide and Hydroxyl Radical Formation by Methylene Blue in the Presence of Ascorbic Acid," Radiation and Environmental Biophysics, 1984, vol. 23, pp. 235-243.
Bull et al., "Transmissible Viral Vaccines," Trends in Microbiology, 2018, vol. 26, No. 1, pp. 6-15.
Cagno et al., "Methylene Blue has a potent antiviral activity against SARS-CoV-2 and H1N1 influenza virus in the absence of UV-activation in vitro," Scientific Reports, Jul. 2021, vol. 11, Article No. 14295, pp. 1-8.
Fernando et al., "Obstacle Recognition Based on Machine Learning for On-Chip LiDAR Sensors in a Cyber-Physical System," Sensors, Sep. 2017, vol. 17, No. 9:2109, pp. 1-14.
CDC—The National institute for Occupational Safety and Health (NIOSH), https://www.cdc.gov/niosh/index.htm, Accessed: Nov. 15, 2021, p. 1.
Chemistry Industry, "Emulsifiers," https://www.chemistryindustry.biz/emulsifiers.html, Accessed: Nov. 15, 2021, pp. 1-9.
Citerio et al., "Induced abdominal compartment syndrome increases intracranial pressure in neurotrauma patients: A prospective study," Critical Care Medicine, Jul. 2001, vol. 29, No. 7, pp. 1466-1471.
Cytiva, "Influenza vaccine manufacturing," https://www.cytivalifesciences.com/en/us/solutions/bioprocessing/knowledge-center/influenza-vaccine-manufacturing/, Accessed: Jun. 30, 2021, pp. 1-10.
Dancer, Stephanie J., "Controlling Hospital-Acquired Infection: Focus on the Role of the Environment and New Technologies for Decontamination," Clinical Microbiology Reviews, 2014, vol. 27, No. 4, pp. 665-690.
De Ponte Muller, Fabian, "Survey on Ranging Sensors and Cooperative Techniques for Relative Positioning of Vehicles," Sensors, Jan. 2017, vol. 17, No. 2:271, pp. 1-27.
Dias et al., "COVID-19: Beyond the virus. The use of photodynamic therapy for the treatment of infections in the respiratory tract," Photodiagnosis and Photodynamic Therapy, Letter to the Editor, 2020, vol. 31, pp. 1-2.
Divangahi et al., "Trained immunity, tolerance, priming and differentiation: distinct immunological processes," Nature immunology, 2021, vol. 22, pp. 2-6.
Eickmann et al., "Inactivation of Ebola virus and Middle East respiratory syndrome coronavirus in platelet concentrates and plasma by ultraviolet C light and methylene blue plus visible light, respectively," Transfusion, 2018, vol. 58, pp. 2202-2207.
Evonik, "A Broad Range of Standard, Custom and Specialized Biodegradable Polymers for Medical Applications," https://healthcare.evonik.com/en/medical-devices/biodegradable-materials/resomer-portfolio, Accessed: Nov. 22, 2021, pp. 1-3.
Fecht, Sara, "The First Fully 3-D Printed LEDs are Here," https://www.popsci.com/article/technology/first-fully-3-d-printed-leds-are-here/, 2014, Accessed: Jun. 30, 2021, pp. 1-4.
Felgentrager et al., "Singlet oxygen generation in porphyrin-doped polymeric surface coating enables antimicrobial effects on *Staphylococcus aureus*," Physical Chemistry Chemical Physics: PCCP, 2014, vol. 16, No. 38, pp. 20598-20607.
Feng et al., "Relative brain displacement and deformation during constrained mild frontal head impact," Journal of the Royal Society Interface, May 2010, vol. 7, pp. 1677-1688.
Fernandez et al., "Singlet oxygen generation by photodynarnic agents," Journal of Photochemistry & Photobiology B: Biology, 1997, vol. 37, pp. 131-140.

(56) References Cited

OTHER PUBLICATIONS

Fracalossi et al., "Singlet oxygen production by combining erythrosine and halogen light for photodynamic inactivation of *Streptococcus* mutans," Photodiagnosis and Photodynamic Therapy, 2016, vol. 15, pp. 127-132.
Gabay, Jon, "Sensor-Based Collision Avoidance Solutions for Drone Fleets," DigiKey, https://www.digikey.com/en/articles/sensor-based-collision-avoidance-solutions-for-drone-fleets, Mar. 2016, Accessed: Jun. 6, 2023, pp. 1-6.
Gahleitner et al., "Sterilization effects on polypropylene: Technology and polymer type effects," TAPPI European PLACE Conference, 2003, pp. 1-7.
Gao et al., "Nano-photosensitizer based on layered double hydroxide and isophthalic acid for singlet oxygenation and photodynamic therapy," Nature Communications, 2018, vol. 9, No. 1, pp. 1-10.
Geeraedts et al., "Superior Immunogenicity of Inactivated Whole Virus H5N1 Influenza Vaccine is Primarily Controlled by Toll-like Receptor Signalling," PLoS Pathogens, 2008, vol. 4, Iss. 8, pp. 1-8.
Gonzalez, Murielle, "Hartalega: Expansion plan on track," Cleanroom Technology, 2019, https://cleanroomtechnology.com/news/article_page/Hartalega_Expansion_plan_on_track/153507, Accessed: Apr. 6, 2022, pp. 1-4.
Hankaniemi et al., "A comparative study of the effect of UV and formalin inactivation on the stability and immunogenicity of a Coxsackievrius B1 vaccine," Vaccine, 2019, vol. 37, Iss. 40, pp. 5962-5971.
Keisuke et al., "Curved acceleration path of ultrasound-driven air flow," Journal of Applied Physics, vol. 125, Article No. 054902, pp. 1-6.
Hasenleitner et al., "In the Right Light: Photodynamic Inactivation of Microorganisms Using a LED-Based Illumination Device Tailored for the Antimicrobial Application," Antibiotics, Dec. 2019, vol. 9, pp. 1-13.
Henneberry, Brittany, "How Surgical Masks are Made," Thomas Publishing Company, https://www.thomasnet.com/articles/other/how-surgical-masks-are-made/, Accessed: Jul. 1, 2021, pp. 1-6.
Hidakawashi Co., Ltd., "Japanese Paper TENGU," https://www.hidakawashi.com/paper-TENGU/index.html, Accessed: Nov. 15, 2021, pp. 1-2.
Hillary et al., "Use of methylene blue and near-infrared fluorescence in thyroid and parathyroid surgery," Langenbeck's Archives of Surgery, 2018, vol. 403, pp. 111-118.
Hiscox et al., "Magnetic resonance elastography (MRE) of the human brain: technique, findings and clinical applications," Physics in Medicine & Biology, Nov. 2016, vol. 61, pp. R401-R437.
Hogan, Quinn H. et al., "Magnetic Resonance Imaging of Cerebrospinal Fluid Volume and the Influence of Body Habitus and Abdominal Pressure," Anesthesiology, Jun. 1996, vol. 84, No. 6, pp. 1341-1349.
Holliday et al., "Concussion: A National Challenge," The Bridge, National Academy of Engineering, 2016, vol. 46, No. 1, pp. 1-132.
Office Communication for U.S. Appl. No. 18/379,863 mailed Dec. 27, 2024, 4 Pages.
Office Communication for U.S. Appl. No. 17/522,811 mailed Apr. 14, 2022, 7 Pages.
Office Communication for U.S. Appl. No. 17/522,811 mailed Jan. 27, 2022, 10 Pages.
Office Communication for U.S. Appl. No. 17/958,639 maiied Aug. 8, 2023, 9 Pages.
Office Communication for U.S. Appl. No. 17/958,639 mailed Apr. 25, 2023, 10 Pages.
Office Communication for U.S. Appl. No. 17/958,639 mailed Jan. 6, 2023, 6 Pages.
Office Communication for U.S. Appl. No. 18/100,993 mailed Jun. 15, 2023, 11 Pages.
Office Communication for U.S. Appl. No. 18/100,993 mailed Oct. 11, 2023, 12 Pages.
Office Communication for U.S. Appl. No. 18/100,993 mailed Apr. 13, 2023, 6 Pages.
Office Communication for U.S. Appl. No. 17/958,639 mailed Nov. 8, 2023, 10 Pages.
Office Communication for U.S. Appl. No. 18/205,082 mailed Nov. 8, 2023, 14 Pages.
Office Communication for U.S. Appl. No. 18/100,993 mailed Dec. 21, 2023, 4 Pages.
Office Communication for U.S. Appl. No. 18/379,863 mailed Dec. 13, 2023, 6 Pages.
Office Communication for U.S. Appl. No. 18/231,922 mailed Dec. 29, 2023, 8 Pages.
Office Communication for U.S. Appl. No. 18/379,863 mailed Nov. 28, 2025, 4 Pages.
Office Communication for U.S. Appl. No. 18/379,863 mailed Feb. 24, 2026, 14 Pages.
Office Communication for U.S. Appl. No. 18/599,518 mailed Apr. 6, 2026, 18 Pages.
Office Communication for U.S. Appl. No. 18/379,863 mailed Jul. 14, 2026, 9 Pages.

* cited by examiner

PHOTOTHERAPY AND PHOTOACOUSTICS

CROSS-REFERENCES TO RELATED APPLICATIONS

This application is a Utility Patent application based on previously filed U.S. Provisional Patent Application No. 63/434,885, filed on Dec. 22, 2022, the benefit of the filing date of which is hereby claimed under 35 U.S.C. § 119 (e) and the contents of which is herein incorporated by reference in its entirety.

BACKGROUND

Light based therapies have been shown to be effective for a number of hyperproliferative medical conditions ranging from cancer to benign skin diseases such as psoriasis. Light based therapies, also known as phototherapeutics, have also been utilized to stimulate or control functions, exemplified for instance, by the use of light to control neurologic functions as known in the field of optogenetics. Light based therapies can require deep penetration of target tissues, on the order of centimeters or more, and thus may entail the utilization of high-power devices such as lasers, with potential safety issues including the risk of unwanted tissue damage. However, the need for high fluence rates due to severe and rapid light attenuation in tissues greatly limits the depth to which light-based treatments can typically be safely and effectively delivered, when light is delivered from an external skin surface. Thus, for some types of light-based treatments such as photodynamic therapy, an invasive procedure is required to insert an optical fiber or fibers, into or proximate to the treatment site, to enable delivery of enough light energy to produce the desired therapeutic effects. Invasive procedures have the risks and downsides of infection, bleeding, pain, accidental organ damage, need for some type of anesthetic or sedation, inconvenience, and off-target side effects. Various embodiments are disclosed herein that enable, directly and/or indirectly, greater therapeutic light energy or its net effects including generation of ultrasound pulses, to be delivered to deep tissues effectively and safely, in a non-invasive manner.

SUMMARY OF VARIOUS EMBODIMENTS

The photoacoustic phenomenon as is utilized in medical practice, is an effect whereby one or more non-ionizing pulsed light beams, which may be convergent at or proximate to the treatment site, are delivered, to create a distal zone of transient, heated tissue, inducing so-called thermoelastic expansion, which in turn generates an ultrasound pulse wave, which may be in the MHz range. The process of thermoelastic expansion occurs by optical absorption by endogenous or exogenously delivered chromophores or substances capable of absorbing light. This photoacoustic signal in the ultrasound range can be useful for in vivo tissue imaging, which comprises its typical medical applications and rather unexpectedly, serve as an activator of a class of compounds known in the art as photosensitizers. Photosensitizers can absorb light and produce singlet oxygen and other reactive oxygen species, and are used for treatment of tumors benign and malignant, against infections, and for treatment of other medical conditions. In addition to light activation, activation of photosensitive compounds or conjugates using ultrasound is also a known phenomenon known as sonodynamic therapy. One aspect of one or more of the various embodiments encompasses the use of tissue penetrating light, which induces beneficial biologic effects, in combination with generation of an acoustic pulse, typically within the ultrasound range, which also has a beneficial effect. The combination of effects can produce a variety of beneficial effects not readily realized by either modality alone, and with the advantage of requiring lower energy transmission through tissue to the target, which improves safety, since external intense light sources and external intense ultrasound sources are not required to enable deep tissue penetration. Another aspect of the one or more of the various embodiments is the delivery of light internally, from an external light source, utilizing water vapor or steam as a light transfer mechanism.

Light energy has been shown to increase adenosine triphosphate (ATP) production which is an absolute requirement for various important cellular functions, including cell repair, and can stimulate cell proliferation important for wound healing. Light therapy is also used to reduce pain, and inflammatory reactions, for example when used as a treatment for painful oral mucositis which can result from various cancer treatments.

Ultrasound energy has also been shown to stimulate tissue repair and healing effects, and can induce beneficial gene expression and protein production, amongst other therapeutic effects.

An additional feature for one or more of the various embodiments alluded to above is the use of water vapor or steam, which may or may not contain other medicaments located within or on the surface of the droplets, or aerosols, which may be passively or actively administered into an internal body cavity such as the mouth, nose, nasopharynx, the upper or lower respiratory tract, gastrointestinal (GI) tract, genitourinary (GU) tract, or by way of an artificially created stoma, or via a pathologic fistulous tract. Steam or liquid vapor can act as a series of photon reflectors or refractors, transmitting light in a confined volume, defined by the steam or liquid vapor stream or track, thus enabling non-invasive light delivery to superficial and deep tissue targets for phototherapeutic purposes. This effect can be seen for example, in commercially available "cold fireplace" apparatuses, whereby light generated and delivered to a water vapor column is confined to the vapor column and used to simulate a fireplace flame. These phototherapeutic purposes can be comprised of photo-biomodulation, photodynamic activation, photo-stimulation, and related known light induced effect. Steam or liquid vapor, which can be comprised of disinfected or purified water, can be aerosolized and inhaled or delivered through the mouth and/or nose, by way of an oral airway tube and/or a nasal cannula, which allows passive or active pressurized delivery of droplets or vapor, or actively inhaled delivery of droplets or vapor. A light source, consisting of one or more light emitting diodes (LEDs), laser diodes, lasers, or related light sources including but not exclusively semiconductor light devices, is used to provide the light to the vapor stream or track, introduced by way of a stoma, natural orifice, or artificial opening or fistula, into a hollow organ such as the oral cavity, the nasopharynx, the upper and lower respiratory tract, and/or the GU or GI tract by way of non-restricting example.

Contemplated light sources and devices in the one or more of the various embodiments can be lensed or configured in such a manner, to concentrate light from one or more external light sources into one or more organ lumen targets. Red light, green light, blue light, near infrared light, infrared light, and other wavebands and wavelengths of light are known to have phototherapeutic effects, due to light absorption by endogenous and/or exogenous chromophores and photosensitizers, and/or by absorption by various cellular components.

Contemplated photosensitizers include but are not limited to exogenous and endogenous substances such as known and contemplated porphyrins, chlorins, texaphyrins, methylene blue and derivatives, erythrosine and derivatives, riboflavin and derivatives, rose bengal and derivatives, protoporphyrin IX, aminolevulinic acid and derivatives, purpurins, curcuminoids, bergamot, psoralens, various photoactive citrus compounds, indocyanine green, and the many other known and contemplated photosensitizers and photocatalytic substances such as titanium dioxide and zinc oxide. Concentrations of at least one photosensitizer can range from 0.001 micromolar to 2.0 molar, or from 0.01% to 2.0% w/v or v/v. Also included in this disclosure is the use of known and contemplated cutaneous optical clearing agents such as mannitol or glycerol, as non-limiting examples, which aid in light and energy transmission through skin. Light and energy can also be transmitted through naturally occurring orifices achieving a photoacoustic effect, such as via the oral or nasal cavity, via the urethra or vagina, and/or the anus.

Also, one or more of the various embodiments may include known and contemplated ultrasonic imaging agents, which are injected intravenously. Ultrasonic contrast agents may be in the form of microbubbles, conjugates, and various types of particles which are echogenic. In addition to increasing the visibility of the signals received by an external ultrasound transducer, the ultrasonic contrast agents can increase the ischemic reperfusion effect, which is included in the one or more of the various embodiments by reacting with the delivered ultrasound energy at the target tissue or surface and increasing the transient closure of blood vessels, stopping or slowing blood flow. The ischemic reperfusion effect is known to induce apoptosis in tissues, and in the one or more of the various embodiments can be used to reduce unwanted tissues such as benign and malignant tumors and cancerous deposits.

Generally, disclosed herein are inventive elements and one or more of the various embodiments as follows:

Light wavelengths and wavebands can range from: the visible (approximately 400-800 nm) to near infrared and infrared spectrum (approximately 800-1350 nm), and even longer wavebands (1600-2500 nm), with red light and near infrared light and longer wavebands preferred for increased tissue penetration. Light pulsing can be accomplished using various light sources including various types of lasers, optical parametric oscillators, laser diodes, light emitting diodes, optionally comprising an array, positioned comfortably on the body, powered preferably by battery power to enhance portability and convenience. A light source array can be arranged such that light is directed in such a way so as to coalesce on a target volume or area of tissue, from different angles and directions, thus reducing the light energy required from any single point on the body, reducing risk of unwanted tissue heating. Light pulse duration ranges from several to hundreds of nanoseconds, and for some applications which include ultrasound imaging as an additional feature, tens of nanoseconds of light pulse duration are preferred, for example when working with a 10-MHz center frequency ultrasound array detector.

Light energy of 0.01 millijoules to hundreds of millijoules per pulse are preferred, delivered externally, though higher energies in the centijoule range per pulse may be useful, and which can be determined and optimized experimentally, using tissue phantoms known in the art, or be determined in vivo. Light energy in the 100-1000 microjoule range is also useful for treatment of very superficial tissue targets, for example on or within the skin surface, or on the internal surface of a hollow organ. The total length of time over which the treatment procedure takes place, number of sessions and duration of sessions within a particular treatment episode, frequency of sessions and related treatment parameters are determined through clinical trials. The treatments being non-invasive and essentially without risk, can be performed on an as needed basis as well, with individual patient experiences guiding the various treatment parameters, leading to personalized, precision treatments. Data from treatments and imaging results, clinical trials and tests, can be captured using smart watches and phones, tablets, laptops, computers, and the like, and uploaded to a central site for analysis, to optimize recommended treatment parameters for individual patients, groups of patients, and populations.

Light energy can be delivered from an array of individual light sources, for example from an LED array which employs an adjustable focusing feature, which enables light to be targeted to various depths, and volumes of tissues. Typical means of focusing light can employ known lenses, mirrors, and mechanical aiming mechanisms, and light intensity and pulsing can be varied using external known means of control and known electronic mechanisms as well.

Combined Photoactivation and Sonodynamic Activation and Real-Time Imaging

Photoacoustic pulse waves can be used to ascertain changes in tissue characteristics, blood flow, tissue volume, and related effects, which reflect the efficacy of the photosensitizer activation by light and ultrasound treatment in real-time. Real-time imaging has major advantages in terms changing the treatment parameters on demand during particular treatment episodes, enabling effects to be modulated and increasing normal tissue protection.

Photoacoustic pulse waves, can in of themselves result in vascular changes, including transient or permanent vessel closure, which can result in cellular apoptosis and tissue reduction. Indeed, vascular effects known in the art include vasospasm and thrombosis, which can lead to tissue ischemia. Reperfusion after transient reduced or cessation of vascular blood flow can compound tissue injury, and in one or more of the various embodiments, as a treatment against cancerous deposits, leading to downstaging of cancer and beneficial immune effects. Cellular apoptosis and other forms of cell death are induced by deliberate induction of tissue ischemia followed by reperfusion, which is known in the field to cause cellular apoptosis, and resultant reduction of tissue volume. Treatment of cancerous or benign tumors in deep or superficial anatomical locations in this manner has the significant advantage of being non-invasive, normal tissue sparing, painless, and lacking of inflammatory and other deleterious off target effects. In the case of cancer, apoptotic cell death induced by the ischemia reperfusion effect can lead to a secondary beneficial immune response, as noted in the cancer immunotherapy art. This important distinction of the one or more of the various embodiments teaches away from high intensity focused ultrasound (HIFU), which is a means of heating tissue to the point of necrosis, which causes pain, inflammation, and which can actually be tumor promoting due to induction of the stereotypic wound healing process involving growth factors and immune cell stimulation, which in this case, has been shown to have potential for enhancing growth of cancerous deposits not completely which are not completely treated.

Ultrasound is defined as sound waves with frequencies greater than 20 kHz.

The ultrasound intensity contemplated to induce ischemia reperfusion is less than 10 W/$cm^2$, with an intensity of 0.01-3 W/$cm^2$ preferred, which is well below the many hundreds of watts typically used for HIFU.

The ultrasound intensity enabling imaging of the ischemia reperfusion effect is contemplated to be in the range of several to dozens (soft tissues) to 100 Mhz (skin/eyes)

The ultrasound energy contemplated for various other biological effects including tissue healing and repair, nerve stimulation, reduction of inflammation and the like is on the order of 0.1-1.5 W/$cm^2$ which is preferred, though ranges higher or lower are not excluded.

Imaging ultrasound is in the general range of several to dozens (for visualizing soft tissues) to 100 Mhz (for visualizing skin/eyes)

Therapeutic ultrasound generally uses frequencies of 1-3 MHz and intensities of 0.5-3 W/$cm^2$.

Pulse-mode delivery may be employed, avoiding tissue damage with higher frequencies/higher energies, which could induce cavitation. Also, the 750 kHz-3 MHz range represent typical ultrasound parameters utilized for physical therapy of injuries and which can reduce inflammation and pain.

Therapeutic nerve stimulation can occur at repetition pulse rates of 1.0-2.5 MHz, at intensities of 0.1-1.5 W/$cm^2$, and ultrasound in the range of 180-650 kHz, with pulse durations of 1-100 microseconds, and duty cycles of 5-50% may be useful as well.

In addition to nerve stimulation, paradoxical ultrasound inhibited nerve conduction for pain and spasticity reduction can be achieved as well, and parameters can be determined experimentally.

Sonodynamic Ultrasound Parameter Examples:

Photofrin and Ti02 is activated by 1 W/$cm^2$ intensity over 2 min or more.

Talaporfin sodium is activated by 0.16 W/$cm^2$, 1 MHz center frequency, 2100 Hz pulse repetition frequency, burst pulse 50% in duty cycle (5000 cycles/burst), 60 seconds.

Some studies have used: 0.5-10 W/$cm^2$, 1-3 MHz for sonodynamic activation.

Multiple types of photosensitizers can be activated sonodynamically, including rose bengal, methylene blue, curcumin, indocyanine green, and others, and are part of one or more of the various embodiments.

ADDITIONAL FEATURES OF VARIOUS EMBODIMENTS

The combination of light induced effects, with or without concomitant ultrasonic stimulation on specific tissue targets can also result in effects such as neural stimulation or suppression, cellular and tissue repair, due to accelerated adenosine triphosphate production, expression of genes leading to production of proteins and other biological substances, and various immune reactions leading to enhanced healing of damaged tissues.

Unlike ultrasound which is attenuated in air or gas filled containing organs and anatomical spaces, light is readily transmitted in a gaseous medium to, or through a solid or liquid tissue where a photoacoustic effect can then occur, proximate or within the target treatment site. Utilized in this manner, both deeply penetrating light, at and above wavelengths and wavebands 800 nm, and into the 2,500 nm range, can be combined with photoacoustic generated ultrasound for tissue stimulation, tissue healing, sonodynamic and photodynamic photosensitizer activation, and for ultrasound imaging.

The advantage of utilizing the ischemia reperfusion effect as an anticancer treatment is that lower energies are required since permanent vascular occlusion is not required, and indeed, ischemia reperfusion teaches away from permanent vascular occlusion required by other anticancer treatments such as high energy radiofrequency ablation, embolization, cryotherapy and the like, which have the downsides of pain, inflammation, and the potential for treatment failure due to downstream tumor promotion due to growth factor secretion and tumor promoting immune effects as secondary consequences of necrosis.

Water vapor, and suspended breathable droplets inhaled into the nasopharynx, upper and lower respiratory tract act as light reflectors, delivering light into hollow organs such as the lungs. Other anatomical routes of vapor or droplet administration utilizing natural orifices or artificially created orifices are also enabled, using pressurized modes of vapor or droplet delivery. Light delivered in this way to internal sites in the body avoids invasive disposition of light delivery devices such as optical fibers.

In one or more of the various embodiments, a photoacoustic device is comprised of one or more LEDs, or one or more laser diodes, which are tunable in the visible light spectrum, and controllable in terms of light intensity, light pulse frequency, and which are arrayed, so as to maximize light delivery to a tissue volume or surface area while minimizing light energy absorption by non-target tissue in the light path. This feature minimizes unwanted heating in non-target tissue. Targeting light in the near infrared range for example, enables tissue penetration from 1 mm to 10 cm as is known in the art. The generation of an acoustic pulse can affect injured tissues or abnormal tissues in various ways, ranging from reduction of inflammation, with promotion of tissue healing, to vascular injury leading to an ischemia reperfusion effect, which can be used to reduce the size and volume of cancerous deposits, while promoting antitumor immune stimulation due to tumor antigen release.

Also, in one or more of the various embodiments, a photosensitizer is administered locally or systemically, and activated simultaneously by light absorption and by the sonodynamic effect, at a target site, in this case cancer, using both known anticancer treatments, which may act synergistically.

Additionally, in one or more of the various embodiments, the treatment effect is monitored in real-time by an incorporated or independent ultrasound transducer, which can image changes in echogenicity and changes in blood flow using power doppler or color flow doppler as an example. This feature permits real-time feedback as to the efficacy or treatment and permits adjustments of the light intensity and pulse train component of the photoacoustic treatment, to increase the acoustic pulse effect causing the ischemic reperfusion injury, as well as the photodynamic and sonodynamic therapy effect.

In yet one or more of the various embodiments, light is delivered using one or more optical fibers, inserted into the lumen of a hollow organ, by way of a naturally occurring orifice, or a fistula, or a stoma for treatment of the lungs, urethra, ureters, bladder, gastrointestinal tract, oral cavity, and nasopharynx, and auditory canal, as non-limiting examples.

In one or more of the various embodiments, an optical clearing agent such as mannitol, glycerol, polyethylene glycol (PEG), polypropylene glycol, dimethylsulfoxide (DMSO), optionally with hyaluronic acid is applied as a topical agent to skin, with other known clearing agents including glucose, dextrose, fructose, sucrose, sorbitol, xylitol, propylene glycol, butylene glycol, ethanol, oleic acid, sodium lauryl sulfate, azone, and thiazone. The formulations of optical clearing agents can range from 1 part agent to 0.0001-100 parts solvent, such as water, or a known skin penetration enhancer such as DMSO, ethanol, hyaluronic acid, and the like.

In one or more of the various embodiments, the use of an optical clearing agent topically applied the skin one hour or less prior to positioning of the light source(s) enhances light penetration intensity and depth in tissue, thus enhancing the phototherapeutic effect, the sonodynamic effect, and the photoacoustic effect as desired.

In one or more of the various embodiments, the photoacoustic device is used in the ultrasound only mode, and/or the light delivery mode only, and/or in the photoacoustic mode, to stimulate stem cell and/or progenitor cell proliferation and function, such as enhanced cell homing, where the stem cells may be naturally in situ, or deliberately harvested and proliferated and differentiated into specific tissues.

In one or more of the various embodiments, external light sources of different wavelengths or wavebands are used to generate photoacoustic pulses at varying depths, creating a "stacked" series of ultrasonic tissue pulses enabling deeper penetration of the photoacoustic pulses, for example, by combining 800 nm and 1064 nm light emitting diode focused arrays on a deep tissue target, whereby the photoacoustic pulses generated at the differing focal points, which vary according to tissue scattering and absorption characteristics, are able to penetrate well beyond the light focal points.

In one or more of the various embodiments the stacking of ultrasonic pulses is optimized by using tissue phantoms known in the art.

In one or more of the various embodiments, treatment related data, including ultrasound imaging data, user and patient or subject feedback is captured and recorded for analysis to improve patient or subject outcomes, for clinical and experimental purposes, and for cost benefit type of analysis.

In one or more of the various embodiments, the patients or subjects are human or animal, including companion animals, livestock, or animals used in preclinical studies.

In one or more of the various embodiments, light is delivered transcranially using near infrared light known to penetrate the skin, and skull bone to stimulate photoacoustic pulses intracranially, for purposes of improving neural function, reducing neuroinflammation, for photoactivation and sonodynamic treatment of brain tumors, malignant and benign, for treatment of vascular malformations, and other pathologic conditions.

In one or more of the various embodiments, a variety of body areas and tissue targets are stimulated such as the tibial area for treatment of overactive bladder, the vagal branches in the ear to treat dysautonomia, and other central nervous system disorders, and the stellate ganglion to treat cardiac arrhythmias. Further, in one or more of the various embodiments many other body areas and target tissues can be therapeutically stimulated.

In one or more of the various embodiments, light delivered that generates photoacoustic pulses reduces abnormal nerve function causing pathologic conditions such as neuropathic pain, or decreases action potentials in nerves to reduce pathologic muscle spasms.

In one or more of the various embodiments, nerves in any body location for example on the head, can be treated to reduce and relieve neuropathic pain, conditions such as trigeminal neuralgia, occipital neuralgia, migraine, cluster, and other types of headaches, and the like.

In one or more of the various embodiments, remote photoacoustic light delivery to the upper arm is used to relieve headache pain.

In one or more of the various embodiments, infrared and/or near infrared light/focused ultrasound can be aimed from the external occiput towards the occipital horn, imparting light and/or ultrasound energy into the hippocampal region of the brain, for therapeutic stimulation purposes. Another aiming direction point is the foramen magnum, directing therapeutic light and/or ultrasound towards the brainstem.

In one or more of the various embodiments, the photoacoustic device is positioned on the external skin surface proximate to segments of the spinal cord where an injury has occurred, from trauma, tumor compression and invasion, from an infection such as an abscess, or bleeding, such as from an epidural hematoma. Treatment by the photoacoustic device can enhance tissue healing from these pathologic conditions. In one or more of the various embodiments, the photoacoustic effect and/or phototherapy effect, and/or external ultrasound is used as a means of spinal cord stimulation.

In yet one or more of the various embodiments, the photoacoustic device, which delivers focused light from a light emitting diode array as an example, generating serial ultrasound pulses, which can be optionally supplemented or augmented by an incorporated ultrasound transducer. Additionally, the focused light itself adds synergistically or additively to the biological effect which may include wound/injury healing, tissue regeneration, neuromodulation, immunomodulation including upregulation or downregulation of the immune system by way of lymph organ stimulation, including lymph nodes, the thymus gland, and the spleen. In some of the one or more of the various embodiments, the incorporated ultrasound transducer array is used to identify the target tissues and organs, prior to photoacoustic/phototherapy/ultrasound treatment.

In yet one or more of the various embodiments, photoacoustic pulses are generated by a device worn on the fingertip similar to known fingertip pulse oximeters, wherein at least one high intensity light emitting (LED) diode array optionally emitting light at 800 nm or greater, or 1000 nm or greater is used to generate at least one photoacoustic pulse on one surface of a fingertip, which an optional second LED array positioned opposite the first LED array on the opposite side of the fingertip. The light and ultrasound pulses are interrogated and analyzed, optionally using known artificial intelligence (AI) techniques, for detection, characterization, and quantification in serial fashion of pathologic conditions in the blood circulating through nailbed capillaries. These abnormal conditions can include inflammatory cells, tumor/cancer cells, free DNA, free RNA, abnormally present cytokines, biomolecules, and the like. Blood glucose levels, hemoglobin A1c and the like can also be serially monitored in this fashion.

In one or more of the various embodiments, light delivered that generates photoacoustic pulses, in combination with the focused light itself, induces futile cycling in mitochondria, which generate adenosine triphosphate in excess, which ultimately results in caloric expenditure through glucose and free fatty acid utilization. This effect is used for weight loss, preferentially reducing adipose tissue while sparing muscle tissue. When focused on the liver, pathologic fatty liver conditions can be treated including nonalcoholic fatty liver disease, steatohepatitis, and the like.

In one or more of the various embodiments, an ultrasonic contrast agent solution is injected per known protocols, which increases the ability of the external ultrasound transducer array to image the target tissue area, which increases the accuracy of the focused light delivery to the target site. In the case of treatment of benign and malignant tissues, or to close pathologic blood vessels such as vascular malformations, the ultrasonic contrast agent also serves to increase speed of onset, duration, and intensity of the ischemic effect, by way of reaction of the contrast agents with the blood vessel walls and blood constituents.

In another embodiment, the external light source is utilized to reduce adipose tissue deep to the skin by way of increasing futile cycling in the mitochondria, in concert with induction of the ischemic reperfusion effect, which leads to apoptosis of adipose cells, further synergistically acting to reduce the size of the fat deposits, painlessly, avoiding detrimental necrosis, over a period of time.

In another embodiment the photoacoustic treatment parameters and the photoacoustic imaging parameters are different, with the photoacoustic device incorporating light sources such as lasers or light emitting diodes which are tunable or emitting at different fixed wavelengths or wavebands. In this embodiment, as a non-excluding example, the light emitted is in the range of 800-830 nm, which penetrates tissue deeply, enabling treatment of internal tissues with light alone, or which activates a photosensitizer absorbing in this spectral region, such as indocyanine green. After treatment, or sandwiched between or simultaneous to treatment, longer wavelength or waveband light in the range of 1500-2000 nm is used to induce ultrasound pulses/signals in the 1-10 MHz range, detectable by an incorporated or independent ultrasound transducer.

In yet another embodiment, photoacoustic pulses, and/or external ultrasound transducer(s), and/or external light delivery from a light device array may be used to stimulate gastrointestinal peristalsis for non-limiting conditions such as gastroparesis, constipation, post operative ileus, ureteral stones, and the like.

In another embodiment, the photoacoustic pulse generating external array may be comprised of multiple arrays, positioned at more than one bodily site, enabling a focused area or region which increases the intensity of photoacoustic pulse generation as well as the volume of tissue which can be stimulated. In yet another embodiment the ultrasound images, photoacoustic pulses, and light signature from tissue can be captured, recorded, and analyzed using artificial intelligence algorithms, and transmitted using telemetry as desired. Light absorbed within the treated or imaged tissue volume can be interrogated and analyzed using Raman spectroscopy techniques as an example. In another embodiment, images, and light analysis of tissue response is utilized in real-time to adjust treatment parameters as needed. For example blood flow in the treatment volume can be analyzed using colorflow doppler, and in the case of tumor treatment, therapeutic reduction and cessation of blood flow with or without reperfusion can be monitored in real-time and adjusted as desired.

In another embodiment known and contemplated acupuncture points and/or other vital points or meridians can be stimulated with focused light and/or ultrasound external or photoacoustically generated with or without optical skin clearing.

In one or more of the various embodiments, water vapor is generated by steam generators or humidifiers, or ultrasonic humidifiers, or various nebulizers, or vaporizers, which may be portable and battery powered. Generated water vapor or steam may be heated or cooled, and droplet size can range from 0.001 μm to 100 μm, and concentration can range from 0.001-1.0 $mg/m^3$. Droplet or aerosol penetration deep into the lungs down to the alveolar level can occur in the ranges of 0.5-10 μm. In general, water vapor generated around 0.5 μm will penetrate deeper into the lungs, whereas 10 μm size droplets will tend to deposit in the mouth and nose. Thus, the general range of aerosol/droplet size is adjusted for the anatomical target. The water vapor may be transmitted to the nose and mouth by way of flexible tubing connected to a mask worn around the mouth and nose, whereby the mask incorporates the light source generating the desired wavebands or wavelength of light, which will typically be in the red range (approximately 620-780 nm), or in the near infrared range (approximately 780-2500 nm).

Droplet/aerosol/vapor size can be varied using different generation techniques known in the art such as, but not limited to: Nebulizers-ultrasonic wave devices which utilize electronic oscillators, vibrating mesh devices which utilize a mesh or membrane to create a mist, so-called "soft mist" inhalers which employ a spring mechanism and nozzles, and various types of jet nebulizers which use a compressed gas; and Humidifiers-Various devices utilize ultrasound to vibrate water into droplets, spray nozzles using compressed air/water, whereby the droplet/vapor size is varied depending on pressure and nozzle configuration, and steam generators using heat to boil water.

In another embodiment, various excipients or additives are included in the steam or vapor, such as menthol, various known bronchodilators, steroids, antibiotics and antivirals, salt solutions, nitric oxide, and the like.

In another embodiment, photoacoustic impulses optionally combined with external ultrasound transduction delivering ultrasound capable of compressing the dural sac, and/or compressing the venous system transiently exerts pressure to displace cerebrospinal fluid and reduce cerebral venous drainage. The temporary compression serves to prevent or reduce harmful brain movement and deformation within the cranium in the event of a collision, impact, or abnormal injurious head motion. The impending harmful collision, impact, or head movement is detected by a sensing device array which activates the compression device just prior to the harmful event, and therefore prevents or reduces brain injury caused by brain impact with the inner cranial structures.

Traumatic brain injury and concussion are very common adverse events, with millions of patients affected per year globally. Despite improvements in external head protection in the form of helmet design and function which mainly serves to protect the skin and skull, little has been done to prevent or reduce internal brain impact, harmful rotational motion, linear brain movement, and various types of uncontrolled brain stretch and deformation within the cranium resulting in brain cell, axonal injury, and vascular insults which contribute to traumatic brain injury, prevention of which is one of the intents of the one or more of the various embodiments. A large number of adverse events can occur after an impact to, or sudden acceleration or deceleration of the head with or without intracranial brain recoil including brain hemorrhage, coup and contra-coup contusions, compression from epidural and subdural hematoma, axonal injuries, and other brain cellular injury due to tensile, stretch, rotational, compressive, and shear forces, which may be prevented or reduced in severity by the one or more of the various embodiments. After initial injury, a large number of adverse, highly troublesome and difficult to treat secondary events have also been described including metabolic, neurotransmitter, and blood flow and vascular abnormalities, brain edema, hydrocephalus, pathologic brain shifts, increased intracranial pressure, and numerous other deleterious neurologic sequela and psychiatric disturbances, and increased dementia risk including the relatively recently recognized chronic traumatic encephalopathy condition.

The human brain is surrounded by cerebrospinal fluid contained within a dural sac, which provides support and cushioning for the brain within the cranium. A blow to the head, head collision, or a sudden head deceleration, acceleration, rotation, and the like can cause the brain to shift within the cranial vault, transiently displacing the surrounding cerebrospinal fluid which allows the brain to harmfully impact the inner dural surface which abuts the inner table of skull, as well as other fixed intracranial structures such as the falx or tentorium. The surface and the interior of the brain can suffer from contusions, hemorrhage, swelling and edema, and other forms of physical injury as well as a plethora of other microscopic and biochemical pathologic processes. Additionally, the soft brain tissue can internally deform, rotate, compress, and stretch at the same time, adding to the injury process, which includes shear and many other forms of damage to intracranial cell bodies, axons, and vascular structures.

The use of a neck collar (Myer 2016) has been described which applies pressure on a continuous basis during use, to the jugular venous system ostensibly to provide a measure of brain protection by stiffening the brain tissue and reducing compliance, but has the major potential drawbacks of: 1) Potentially compressing the carotid artery system in addition to the jugular vein system which would be very harmful to normal brain function, 2) Limiting neck mobility which greatly reduces practicality for users engaged in any sort of activity where head motion and change in visual field direction is required, 3) Discomfort from the constant neck compression required when wearing a tight, compressive neck collar, 4) Potential for neck collar dislodgement or rotation, leading to misplaced pressure on the neck surface which could lead to device malfunction and airway compromise if it applies pressure to the trachea for example, and 5) Continuous, sustained reduction of cerebral venous outflow during use which could induce brain vascular congestion causing headaches, visual problems, and a wide variety of other neurologic deficits and problems which could even include cerebral hemorrhage, if the collar is worn on a continuous basis, or if it fits too tightly around the neck.

Airbag devices worn by a user may have been described in the prior art that are positioned around the chest or head and are designed and intended to reduce injury to the user by acting as a cushion. Used in this manner, the airbag devices are in intended to reduce the impact force of a collision and reduce bodily deformation and compression, and reduce sudden head deceleration, which is an entirely different and opposite mechanism of action enabled by the one or more of the various embodiments, which teaches away from prior art, by inducing and enabling torso and pelvic compression, whose intent and purpose is to protect the brain internally by preventing or reducing brain motion relative to skull motion, and to simultaneously stiffen brain tissue, reduce brain tissue compliance, and therefore reduce brain compression, stretching, and deformation, actions not enabled by the cited patents. Some of the prior art describes an intracranial balloon apparatus which can compress the brain, which is in opposition to the one or more of the various embodiments, which teaches away from brain compression using an entirely external system. Also, compression devices for cardiopulmonary resuscitation (CPR) may have been described in the prior art but they differ from the one or more of the various embodiments, in that they are devices not suitable to be worn during activity, are specifically designed and intended to compress the heart repeatedly, and increase brain blood flow during chest compression and increase venous drainage from the brain during chest decompression.

Other prior art references may have described an abdominal compression device intended to increase blood pressure for patients with orthostatic hypotension, using a pump to inflate a bladder, which is a slower filling process which would not enable brain protection due to compression delay, compared to the one or more of the various embodiments which utilizes much faster compressed gas and/or propellant to very rapidly fill a bag, balloon, or bladder just prior to a head impact or related brain injury event.

Also, in addition to incorrect compression activation timing and duration, the prior art does not make obvious or anticipate enabling testing and imaging to optimize compression area, volume, location, depth, speed, and duration, which would enable brain protection intended in the one or more of the various embodiments. Instead, the prior art that tends to treat hypotension due to hemodialysis and related critical care situations with the use of prolonged abdominal compression which may be manually performed, in combination with fluid infusion.

The one or more of the various embodiments detail apparatuses and methods of temporarily displacing cerebrospinal fluid and increasing the intracranial cerebrospinal fluid pressure which can prevent or reduce displacement and shifting of cerebrospinal fluid at a time point just prior to a cranial impact, blow or sudden acceleration, deceleration, or head rotation, thus stabilizing and maintaining the normal brain position within the skull, with concomitant transient stiffening of brain tissue just prior to the likely injurious event, thereby preventing or reducing brain tissue injury from abnormal and pathologic internal brain motion and deformation.

Another aspect of the one or more of the various embodiments is intended to mitigate against blast injury to the brain, which may occur in the combat/military setting. Research has demonstrated that an initial overpressure wave occurs with blasts, such as occurs with bomb detonations, and that the overpressure wave can induce a rapid rise in intracranial pressure. The one or more of the various embodiments enables transient reduction of intracranial pressure, which may mitigate or reduce brain injury from the overpressure wave induced intracranial pressure spike. Many individuals caught in blast situations can experience secondary impact events which are also addressed by the one or more of the various embodiments.

SUMMARY OF VARIOUS EMBODIMENTS

Many different embodiments are possible, and the various embodiments are capable of modification and alteration in many and various respects, all without departing from the scope of the claims. Accordingly, the embodiments, drawings. and descriptions herein are in no way meant to be regarded, or construed, as restrictive.

The one or more of the various embodiments prevent or reduce harmful brain movement and deformation from what would be an otherwise injurious head impact, collision, sudden acceleration, deceleration, or rotational brain movements. Protective devices and equipment have been described and developed that seek to protect the head, by utilizing cushioning external to the head which reduces deceleration. Unfortunately, these products mainly reduce scalp injuries and skull fractures, and the brain can still move abnormally, collide with the inner skull surface lining, and deform harmfully within intracranial space. Numerous studies have demonstrated the inability of helmets and external cushioning devices to prevent concussions and prevent traumatic brain injuries, and in fact, the more forceful the blow and impact to the head, the more likely that a concussion or traumatic brain injury will occur, despite the use of a helmet. For example, in the National Football League of the US, hundreds of new concussions are documented to occur each season, despite the use of state of the art helmets, and the cumulative brain injury effects have been shown to result in chronic traumatic encephalopathy, a devastating and severe type of dementia. The primary reason for the inability of helmets to prevent concussions is that helmets and related devices developed to date cannot prevent the internal brain movement that continues to occur relative to the inner skull, and within the accelerating or decelerating cranial vault, due to the fact that the brain remains in motion within the skull due to the separation of the brain from the skull by cerebrospinal fluid, such that even if the head is decelerating after an impact, blow, or whiplash, injurious brain movement occurs. The dyssynchronous movement of the brain relative to the skull causes uncontrolled brain tissue rotational motion, and forward and backward brain movement, with abnormal tissue shifting and compression, causing the brain and brain stem to rotate, stretch, and otherwise deform harmfully, as well as collide with the inner dural skull lining abutting the rigid inner skull surface and recoil, sometimes multiple times.

In contrast, the one or more of the various embodiments comprise apparatuses and methodologies which are capable of reducing and even preventing internal abnormal and harmful brain motion and deformation entirely. The one or more of the various embodiments and methodology enables brain protection by inducing rapid and transient intracranial cerebrospinal fluid displacement and pressure increase, just prior to the potentially injurious event, resulting in maintenance of cerebrospinal fluid volume, distribution, and compartment shape within the cranial vault, thus in essence cancelling out the effect of the differential brain-cerebrospinal fluid density which has been demonstrated to be approximately 1.046 for brain with cerebrospinal fluid density being approximately 1.00 (Babbs 2004). In other words, if the effective density of cerebrospinal fluid were to approximate that of the brain, there would essentially be no acceleration of the brain relative to the cerebrospinal fluid.

The one or more of the various embodiments may be designed to rapidly shift cerebrospinal fluid within the spinal dural sac in the lumbar and/or upper cervical and/or foramen magnum area/and or the cerebral venous drainage pathway anywhere from the intracranial compartment to the pelvic compartment or the spinal compartment toward the closed intracranial compartment which can result in a rapid, transient increase in intracranial cerebrospinal fluid pressure, which can in turn reduce brain motion due to head impact, sudden deceleration or acceleration, or rotation.

Further, the one or more of the various embodiments may induce a sudden rise in CSF pressure enabled by at least one external ultrasound generating device, which compresses for example, the lumbosacral thecal sac, which has been demonstrated to be a mechanism which can shunt cerebrospinal fluid from the spinal subarachnoid space toward the cranial cerebrospinal fluid compartment, increasing the intracranial fluid pressure which would tend to stabilize and fix the brain in its normal resting position relative to the inner table of the skull. Thus, the external cerebrospinal fluid cushion surrounding the brain and the internal intraventricular spaces which are also filled with cerebrospinal fluid are maintained by way of increased fluid pressure. This process reduces or precludes the movement of the brain towards the inner table of the skull that occurs when sudden head deceleration or acceleration occurs from collisions, crashes, and impacts, all of which are known to cause brain injuries, including coup and contracoup injuries and intracranial bleeding. Prevention or reduction of initial brain movement can also reduce or dampen secondary brain recoil, which is also injurious. Also, abnormal and harmful brain rotation and brainstem injury and other types of brain deformation may be prevented or lessened as well. The sudden shift of cerebrospinal fluid intracranially raises the intracranial pressure only transiently if the intra-abdominal CSF pressure increase is very transient as well, a process which is safe and well tolerated and enabled by the one or more of the various embodiments' design and function.

In addition to movement of cerebrospinal fluid towards the intracranial compartment, another key brain protection feature of the one or more of the various embodiments is that a sudden and transient increase in intra-abdominal pressure which is enabled, for example by ultrasound transmission affecting the venous compartment, which is normally very low, sub-atmospheric to less then 7 mmHg, with optional increased intra-pelvic pressure via the venous system in the pelvis, causes the diaphragm to be displaced upwards, which in turn increases intrathoracic pressure. This causes an increase in central venous pressure compressing the inferior vena cava resulting in reduced venous return to the heart via the jugular veins which in turn transiently reduces venous return from the brain. A temporary reduction of venous outflow in absence of decreased arterial inflow enabled by the one or more of the various embodiments and this process also transiently increases the internal stiffness of brain tissue, a phenomenon which can reduce the tendency for harmful brain deformation and movement to occur from blows to head, blast injuries, or sudden head deceleration, acceleration, and rotation. The brain is one of the softest solid organs, and prevention of internal and superficial brain deformation or sloshing can prevent direct brain cellular injury and damage, axonal stretching, shearing, and other similar adverse phenomena. Thus, the one or more of the various embodiments provides for brain protection from head trauma by way of at least two mechanisms, namely a rapid and transient increase in intracranial cerebrospinal fluid pressure which maintains normal brain position and reduces or precludes uncontrolled intracranial movement, and a transient reduction in venous outflow due to distal venous compression from the jugular venous system which temporarily stiffens the brain, reducing brain tissue compliance, a process which has been demonstrated to be a protective mechanism due to reduced harmful brain tissue rotation, shearing, stretching, compression, and the like.

The rapid, transient, and non-harmful increase in intra-abdominal pressure with an optional increase in pelvic pressure in the one or more of the various embodiments may also be enabled by the use of a specially designed abdominal binder, corset, or belt which encircles the abdomen at least partially, and may also be held in proper position by use of at least one optional shoulder strap. The binder, belt, or corset in one embodiment is entirely or partially rigid or entirely or partially flexible. In one embodiment the rigid segment of the belt, binder, or corset is fitted to the user's back, while the flexible segment conforms to the anterior abdominal wall. The flexible segment may be comprised of a polymeric substance such as nylon, or a metallic substance and construct such as a chain mail configuration, which allows for user torso movement, but is not stretchable, and thus is designed to permit a sudden, controlled, transient compressive force against the abdominal wall and optionally the pelvis, for example using an expanding balloon incorporated into the anterior or anterolateral aspect of the device, which temporarily compresses the abdominal and optionally the pelvic cavity, resulting in a transient, rapid shunting of lumbosacral spinal cerebrospinal fluid into the intracranial subarachnoid and intraventricular space. The polymeric balloon can be rapidly expanded using compressed gas contained in a small cylinder or similar container such as a $CO_2$ cartridge, or the expanding gas within the balloon can be rapidly generated chemically as occurs in automobile crash protection airbags. The gas is rapidly vented through preexisting holes in the balloon such as occurs after automobile airbag inflation.

In one or more of the various embodiments the structure surrounding the abdomen may be entirely rigid which also allows for all of the anterior compressive force to be transmitted against the abdominal wall. This construct also optionally incorporates a protective outer shell, which shields the device from direct impacts, which could damage or prematurely trigger the compressive device. In yet another embodiment a belt-like structure tightens rapidly and reversibly, which temporarily constricts the abdominal wall, raising the intra-abdominal pressure transiently. This belt movement which transiently constricts and compresses the abdomen can be accomplished using a high speed motor incorporated into a winding mechanism which tightens the belt transiently by rolling it into a cylindrical configuration, and allows for rapid active or passive release of the tightened belt construct as well, which decompresses the abdomen. In all device compression embodiments, the rapid but reversible abdominal and optional pelvic compression only occurs when imminent impact or blast is sensed using accelerometers, ultrasonic, electromagnetic, or infrared movement detectors, and/or pressure detectors, which may be all included in the one or more of the various embodiments. In other words, the compression device may be activated just prior to the impact, collision, or other harmful head movement event. The compressive force on the abdomen and optionally the pelvis occurs at an interval of several seconds or less before the harmful head injury event, allowing for enough time for lumbar cerebrospinal fluid shift towards the intracranial compartment and brain tissue stiffening from reduced jugular venous drainage to occur.

The lumbar cerebrospinal fluid volume and timing of shift toward the intracranial compartment and subsequent movement extracranially back into the lower spinal compartment can measured and ascertained using spinal MRI or myelography (Hogan 1996). These types of measurements can be used to optimize the speed, degree, and duration of abdominal and optional pelvic pressure needed to shift an adequate volume of cerebrospinal fluid which generates an adequate increase in cerebrospinal fluid pressure. Additionally, cerebrospinal fluid motion can be optionally assessed using the time-spatial inversion pulse (Time-SLIP) method which makes it possible to directly visualize the flow of cerebrospinal fluid using MRI (Yamada 2014).

The one or more of the various embodiments may contemplate that the variables and parameters of device induced abdominal compression can be optimized by direct measurements and visualization of cerebrospinal fluid movement from the thecal sac towards the intracranial space in clinical tests which may include imaging of motion and position of the brain, spinal cord, and cerebrospinal fluid. The variables and parameters that can be tested include abdominal venous and/or CSF compartment compression timing, speed, pressure, duration, and optimal location of the force applied to the abdomen. Likewise, the resolution parameters of compression can be similarly optimized. Injury to the abdomen is prevented due to limitation of the compressive force, degree of compression, and the transient nature of the compression, as well as the use of multiple focused ultrasound generation devices, which reduces the force imparted in one particular pathway. In addition, after determination of optimal compression parameters, the volume, shape, and surface area of the device component that accomplishes the bodily compression is determined, and the design and manufacture of the device component limits the expansion and degree of compression to further insure safety. In another embodiment, the compressive device incorporates a pressure sensor with automatically adjusts and regulates the abdominal compressive force to remain within a certain predetermined limit or to reach a certain predetermined degree of pressure.

The degree of brain stiffness induced by abdominal and optional pelvic compression which resists abnormal harmful brain rotation, whiplash movements, and deformation can be assessed using MRI elastography (Hiscox, 2016). The one or more of the various embodiments may contemplate that the intra-abdominal compression parameters sufficient to result in optimal brain protection can be ascertained by performing MRI elastography, by comparing brain stiffness with and without intra-abdominal compression, in an individual user, or in groups of users. In addition, diffusion tensor MRI and other techniques have been used as a surrogate measure of brain injury in before and after studies testing various venous cerebral drainage obstruction interventions (Myer et al 2016). Mathematical and computerized simulations of concussion and brain injuries, as well as phantoms and crash dummies, and other in vivo and in vitro models are also known in the art as means of testing brain protection interventions as well, and can also be optionally utilized to evaluate and optimize the design and compression parameters of the one or more of the various embodiments (Martin 2016, Holliday 2016, Wojnarowicz 2017, Ng 2017, Post 2017, Li 2015).

The abdominal binder, belt, or corset compression device is custom fitted to the user or is adjustable in diameter and tightness for example using a buckle, rachet, or clasp as is commonly employed in pants belt to insure maximal comfort and to minimize interference of normal lumbar and lower thoracic spinal movement. The tightness of the compression device can be optimized using an incorporated pressure sensor which communicates to the user the optimal degree of resting tightness. The binder, belt, or corset is optionally comprised of breathable material such as vapor permeable nylon or a perforated more rigid shield to reduce heat buildup and sweating on the abdominal surface, and may also utilize a flexible but inelastic material which deforms with abdominal movement but buttresses the expanding or abdominal pressure component of the device which leads to abdominal compression and a desired rise in intra-abdominal pressure. The mechanism that induces transient abdominal and optional pelvic compression can further be comprised of either a compressive polymeric bladder, balloon, or bag that is reversibly filled with air or a fluid using a high speed pump, compressor, a cylinder or container of compressed inert gas such as $CO_2$·nitrogen, or argon gas, or a cinching belt-like mechanism whereby a band is rapidly tightened then loosened, and in yet another embodiment utilize at least one spring contacting a rigid, contoured plate in contact with the anterior abdominal wall which is maintained in compression then rapidly allowed to extend and retract to transiently compress the abdomen. In all cases the increase and decrease in intra-abdominal pressure is such that abdominal organ injury is avoided.

The range of transiently increased intra-abdominal pressure induced by the one or more of the various embodiments may be between the range of 1 mmHg to 50 mmHg, and is adjustable and customized for the user's size, weight, anatomy, and expected degree of required cerebrospinal fluid displacement. The intra-abdominal compression process is very rapid and occurs over a period of 1 millisecond (ms) to 1 second (sec) followed by immediate decompression occurring over a period of 1 ms to 1 sec. Optionally, the compression can be maintained for a period of 1 ms to 2 sec followed immediately by rapid decompression over 1 ms to 1 sec. Also, a pressure sensor is optionally incorporated into the abdominal compression device which senses and serves to regulate the desired compressive force, prior to, and during activation of the compressive device, and is optionally adjustable to accommodate differences in abdominal anatomy, size, shape, and volume. If desired, the abdominal compressive force is adjusted for the individual user in advance of activation, allowing for differences in abdominal anatomy, shape, size, volume, and desired degree of compression. For example, the degree, speed, and duration of abdominal compression required for brain protection in a soccer player who heads the ball, or a football player who may suffer a concussion, and may be different from a recreational bicyclist versus a user who rides a high speed motorcycle.

Correct and accurate activation of the abdominal compression and optional pelvic compression device and/or at least one ultrasound generating external device is enabled by use of a helmet, headband, or similar flexible or adjustable headgear, incorporating at least one or an array of pressure sensors, impending impact sensors, and/or motion sensors which may utilize ultrasound, infrared light from light emitting diodes, radar, lidar, or be electromagnetic, and/or at least one or an array of accelerometers and/or gyroscopes, and/or GPS or global positioning system locating devices, which detect impeding harmful head impacts, collisions, brain and head rotation, acceleration and deceleration events, with the events relayed to the compression device leading to activation of the brain protection mechanism just prior to the potentially harmful event. Pressure sensors, and/or accelerometers, and/or gyroscopes, and/or GPS, and/or ultrasonic, and/or infrared, and/or electromagnetic motion detectors collectively known as sensing devices may also be worn on the neck, torso, located in a mouthpiece, or on other body locations or even separate from the body on a cycle, vehicle, or other conveyance to detect impending or potential sudden head impact, body and head deceleration or acceleration.

Pressure sensors and/or accelerometers and/or gyroscopes and other collision and motion detector devices may also be incorporated into an object or conveyance utilized by the user, which may or may not be directly in physical contact with the user, with activation of the abdominal compression device accomplished by way of a directly wired or wireless connection, with data integration optionally occurring by way of a central processing unit or CPU which controls the activation of the compression device.

In a similar fashion, machine vision, imaging, and machine learning technologies and devices, radar, and the similar detection apparatuses such as those used in moving vehicles (Castano 2017, Navarro 2016, Muller 2017), can be used in a similar fashion to ultrasonic collision warning sensors or infrared or electromagnetically based collision or movement detection technologies and can be employed in the one or more of the various embodiments and are optional means of impending collision and impact sensing as well. Other collision detection systems that are optionally a part of the one or more of the various embodiments include radar or laser collision detection devices. In all embodiments where collision, impact, or abnormal head movement is detected, the sensing devices are powered by disposable or rechargeable batteries incorporated into the devices. One embodiment accomplishes rapid abdominal wall compression by way of at least one flexible, expandable bladder, balloon, or bag mounted on a rigid or flexible but not stretchable polymeric band which is connected to a compressed gas container or propellant container which rapidly produces expanding gas, or transfers compressed gas rapidly in 100 milliseconds or less to the bladder or balloon which compresses the abdomen. The compressed gas is preferably inert, non-toxic, and the propellant is preferably non-toxic, and is contained within at least one polymeric or metallic container incorporated into the device.

In another embodiment the propellant is contained within the expandable balloon, bladder, or bag. Just prior to the initiation of head contact, at least one pressure sensor and/or accelerometer or other detection device is activated and causes rapid release of the gas or generation of expanding gas into or within the bladder or balloon which causes rapid external abdominal wall compression, inducing a sudden rise in intra-abdominal pressure with resultant temporary shift of cerebrospinal fluid towards the intracranial subarachnoid and ventricular space, and transient reduction of cerebral venous return. These processes result in stabilization of the brain relative to the inner table of the skull by preventing or reducing cerebrospinal fluid shifts, and increase brain stiffness which reduces or prevents brain cell damage and axonal stretch injury and disruption by reducing or preventing brain deformation, rotation, and sloshing. The expanded gas is rapidly vented though openings in the bladder or balloon into the ambient air, as in a vehicular airbag, or by way of a gas release valve as is utilized in some airbag vests, which results in rapid return of the intra-abdominal pressure, intracranial pressure, cerebral blood flow, and cerebrospinal fluid dynamics back to normal range and location, as the impact force is dissipated or the harmful event passes.

In another embodiment, more than one gas expansion event is enabled in rapid succession by use of multiple contained gas or propellant devices, to address the need for more prolonged brain protection in the event of detection of multiple successive potentially injurious events, or where secondary brain recoil requires prevention.

In another embodiment, at least one of the bladder or balloon is filled with compressed ambient air contained in at least one cylindrical container, and at least one pump enabling refilling of at least one cylindrical container is part of the device system enabling prompt reuse. This embodiment could be used in activities or sports such as football, soccer, boxing, skiing, or any other sport, competition, or activity including martial arts or combat where brain injuries are known to occur, where the device could be reset between plays or events, as required or when convenient. The air pump can be employed manually, or in an automated mode after brain protective release of the gas into the bladder or balloon ensemble. A variant of this embodiment would utilize at least one compressed gas container which is single use, for instances when refilling is not practical, for example during a combat situation. Incorporating multiple compressed gas containers which may optionally be cylindrical in shape, into the compression device allows for multiple abdominal compression device activation sequences without the need to refill between use.

In another embodiment the abdominal compression mechanical or ultrasound device is incorporated into body armor, on the anterior inner surface of the armor which abuts the abdomen, thus shielding the device from projectile or blast damage and accidental inappropriate device activation. This embodiment is intended for use by individuals who may be more likely to be exposed to such hazards, such as military or law enforcement personnel. Further, in a related embodiment, the abdominal compression device is incorporated into an article of clothing abutting the abdominal area, with the compression device in contact with the anterior abdominal wall. Another variant of the abdominal compression device is protected on its external aspect by a rigid polymeric shell, or sufficient dense padding which precludes inadvertent device activation or damage to the device by a blow to the abdominal region, that may occur while playing football as an example.

In yet another embodiment the abdominal or ultrasound compression device is incorporated into a seatbelt or lap belt such as would be commonly found in a vehicle such as an automobile, truck, airplane, or related conveyance. The abdominal or ultrasound compression device is correctly positioned over the user's abdominal region when the seatbelt or lap belt is fastened, and reduces risk of brain injury from head impacts or whiplash due to vehicular collisions or sudden braking or stops. This embodiment can be utilized along with a standard vehicular airbag protection system, and the abdominal or ultrasound compression device can be optionally activated at the same time as the airbag. Further, in another related embodiment the expanding gas which inflates the airbag also inflates the abdominal compression construct or activates the ultrasound device which is incorporated into the seatbelt apparatus.

In another embodiment a high speed flat motor rapidly winds a strap mechanism which transiently squeezes the abdomen, rapidly increasing the intra-abdominal pressure, followed by immediate release of the mechanism which rapidly relieves the pressure. In yet another embodiment, a roller which conforms to, and exerts pressure on the anterior pelvis or lower abdomen, when activated moves rapidly by rotation around the long roller axis in a caudal to cephalad direction, essentially milking the cerebrospinal fluid in the lumbar dural sac in an upward direction, increasing the intracranial cerebrospinal fluid pressure and brain stiffness transiently.

In another embodiment, abdominal and optional pelvic compression can also occur from a combination of mechanical compression by pressure from an expanding bag, balloon, or bladder, together with a squeezing action on the abdomen caused by a transient tightening band or belt-like apparatus around the abdomen. In yet another embodiment, compression of the torso and pelvis can be accomplished by an expanding bag, balloon, or bladder which abuts a rigid or semi-rigid polymeric plate which conforms to, and in in contact with the anterior or anterolateral pelvis, abdomen or thorax, spreading the compression force over a broader area than would be encompassed by the bag, balloon, or bladder alone.

In another embodiment, a pressure sensor incorporated into the compression apparatus indicates to the user the optimal pre-activation degree of tightness and snugness of fit of the abdominal, pelvic, and thoracic compression devices. Furthermore, the pressure sensor can also be utilized to regulate and adjust the degree of abdominal, pelvic, and thoracic compression that occurs with device activation, to optimize cerebrospinal fluid displacement and brain stiffening, as well as to prevent injury to the abdomen, pelvis, or thorax by excessive compressive force.

Collision, impact, and injurious movement prediction algorithms based on motion detection of the user's head and/or body, or by object, projectile, or pressure detection in the surrounding environment, can optionally be a part of the one or more of the various embodiments as a means of enabling correct timing of device activation and degree of abdominal with optional pelvic compression that leads to effective cerebral protection. Collision, impact, and movement related data from the sensing devices can be collected and integrated by a CPU or central processing unit which is optionally a part of the one or more of the various embodiments, which enables correct timing of abdominal and optional pelvic compression just prior to the potentially injurious event. Another embodiment utilizes a lanyard or cable which connects the user to conveyance such as a bicycle, a motorcycle, or an animal such as a horse or donkey such that the compression device is triggered in the event of a sudden separation or fall of the user from the means of conveyance.

In yet another embodiment, a multifaceted warning system is enabled by multiple sensing device arrays which communicate wirelessly between a primary user defined as an individual about to experience a harmful brain injury event, a secondary user who may be a contributor to that event which can cause impending brain injury affecting the primary user, a moveable or moving object in the immediate environment of the primary user, and/or a fixed non-moveable location, in any combination or permutation. Examples include two users engaging in American football, where a primary user wearing a sensing device array carrying a football is about to be tackled by a secondary user also wearing a sensing device array, and where the sensing device arrays from each user relays data to the primary user's CPU that a harmful impact to the head and brain of the primary user is imminent. The primary user's CPU integrates the impending impact and collision data and determines that brain harm is imminent and activates the primary user's compression device. Further, in a related embodiment, the football field itself can also be equipped with a sensing device array which monitors impending collisions and contributes data regarding impending brain harming collision, impact, or abnormal uncontrolled head movement such as whiplash type movements. The stationary sensing device array serves to relay additional probable collision and impact data which contributes to brain injury prevention or reduction in a complex multi-user environment.

Also, in another somewhat similar sports environment, soccer players who may head the soccer ball may be equipped with sensing devices worn by each player. The soccer ball itself also incorporates a sensing array which communicates with the user sensing device enabling the CPU worn by the user to determine when the compression device should be activated to prevent or reduce harmful brain motion and deformation resulting from head impact with the soccer ball. In addition to events leading to concussions and traumatic brain injuries, impending subconcussive events which have been defined as events similar to those which give rise to an overt concussion but with less force and acceleration/deceleration (Slobounov 2017) capable of causing cumulative brain harm, can occur hundreds or thousands of times over a single competitive season, for example in American football, and can be detected and the compression device activated appropriately multiple times in yet another embodiment.

In another embodiment, thoracic compression may be 1 millisecond to 1 second after abdominal compression in a sequenced, predetermined, pre-programmed fashion, optionally regulated by an incorporated CPU. This embodiment maintains the brain protective cerebrospinal fluid shift from the lumbar compartment towards the intracranial compartment, as well as reducing venous return from the brain inferiorly, thus reducing brain compliance which is also brain protective. Thoracic compression is enabled by utilizing the same variety of apparatus and methods as described for abdominal compression. In one embodiment the thoracic compression is accomplished using a bag, balloon, or bladder which exerts transient compression against the sternum when inflated by compressed gas or a propellant substance. The sternal compression depth is between 1 to 8 cm. The range of transiently increased intra-thoracic pressure induced by the one or more of the various embodiments is between the range of 1 mmHg to 50 mmHg, and is adjustable and customized for the user's size, weight, anatomy, and expected degree of maintenance of required cerebrospinal fluid displacement. The intra-thoracic compression process is very rapid and occurs over a period of 1 millisecond (ms) to 1 second (sec) followed by immediate decompression occurring over a period of 1 ms to 1 sec, by way of a gas release valve or openings in the bag, balloon, or bladder. Optionally, the compression can be maintained for a period of 1 ms to 2 sec followed immediately by rapid decompression over 1 ms to 1 sec. Also, a pressure sensor is optionally incorporated into the thoracic compression device which senses and serves to regulate the desired compressive force, and is optionally adjustable to accommodate differences in thoracic anatomy, size, shape, and volume.

In one embodiment, the abdominal and optional pelvic and thoracic compression or ultrasound device is integrated into a vest, shirt, or protective garment such as body armor, which encompasses the thorax and abdomen. The garment can be flexible but not elastic, which allows for user movement such as torso flexion, extension, lateral bending, and rotation, along with effective abdominal and thoracic compression.

In another embodiment a high speed flat motor rapidly winds a strap mechanism which transiently squeezes the thorax, rapidly increasing the intra-thoracic pressure, followed by immediate release of the mechanism which rapidly relieves the pressure.

In yet another embodiment the thoracic compression or ultrasound device is incorporated into a shoulder belt or harness such as would be commonly found in a vehicle such as an automobile or a truck, or in a related conveyance. A combination of a seat belt and torso harness such as may be found in a baby or child car seat restraint system can also incorporate compression or ultrasound devices which are triggered in advance of a collision or a sudden stop to provide brain protection, especially useful in prevention or reduction of brain injury due to whiplash types of head motion.

In another embodiment the various embodiments is utilized in combination with other protective devices and equipment that are intended to act as a cushion during a collision, for example in combination with an airbag vest and/or an airbag helmet, or in combination with vehicular mounted airbags. The one or more of the various embodiments can also be used in combination with any head trauma protective gear, such as helmets, protective facemasks, neck collars and braces, protective garments, body armor, external cushion airbags, or any sort of protective gear which is intended to reduce harmful bodily impact forces and head deceleration.

In yet another embodiment, a compact, self contained miniature sensing device array and CPU incorporates a small portable battery power supply and is comprised of at least one of a magnetic sensor device (Wu 2017), radar device (Moses 2011), inertial sensor (accelerometer, gyroscope), pressure sensor such as a piezoelectric sensing device, infrared and ultrasound detectors (Gabay 2016), and related technologies that are used along with a CPU which captures, integrates data, and activates at least one compression device. The self-contained system can be manufactured in quantity and adapted for multiple environments, uses, and incorporated into head gear, garments, belts, various objects such as sports equipment such as soccer balls, conveyances such as bicycles, safety equipment such as seatbelts, and the like.

In another embodiment, brain injury from blasts can be mitigated by a device induced drop in intracranial pressure and simultaneous increase in venous return from the brain towards the heart, which is transient. This process is enabled by abdominal and optional pelvic decompression, by way of a suction device affixed to the abdomen and optionally the pelvis. The relatively low profile suction device is optionally dome shaped, and a vacuum can be rapidly generated within its interior using at least one vacuum cylinder or container, or at least one ultra high speed pump. The suction device is affixed to the abdominal wall and optionally the pelvic wall anteriorly, and is triggered upon detection of a blast wave. Suction on the anterior body wall reduces the intra-abdominal pressure suddenly and transiently. This action mitigates the sudden increase in intracranial pressure caused by the action of the overpressure blast wave on the brain. Cerebral stiffness is also simultaneously and transiently decreased, which can add a measure of brain protection from the blast. This embodiment may also incorporate a compression device, which then raises the intracranial pressure and decreased brain tissue compliance transiently, which is protective against brain impact and/or deformation which also commonly occurs in blast situations, as a secondary phenomenon.

In one embodiment, an ultrasonic pressure wave is transiently generated by at least one external ultrasonic transducer/and or at least one external photoacoustic device, aimed at the venous drainage system in the pelvis/and or abdomen, and/or at the lumbosacral dural sac, leading to a transient compression of said structures. Compression of said structures over periods ranging from 1 to 100 milliseconds to 1000 milliseconds to 5000 milliseconds leads to stiffening of the CSF column which impedes or prevents brain motion from abnormal harmful movement. In yet another embodiment, the ultrasonic pressure wave is sequentially generated starting in the lumbosacral region and moving superiorly towards the abdomen and then optionally to the thorax, resulting in a more prolonged compression of the CSF column. Ultrasonic pulses can range from at least one or more cycles of less than 2 Hertz (Hz) to between 2 and 100 Hz, to 100 to 1000 Hz, from 1000 Hz to 500 kHz with high peak pressures ranging from 1 to 30 Megapascal (MPa), to 30 to 200 MPa, or more, with at least one pulse lasting from 1 microsecond to 500 microseconds, to one second. In various cases, experiments using known in vivo and in vitro brain movement and brain injury models and experiments may be used to optimize the parameters and internal body targets.

BRIEF DESCRIPTION OF DRAWINGS FOR VARIOUS EMBODIMENTS

Figure 13A:
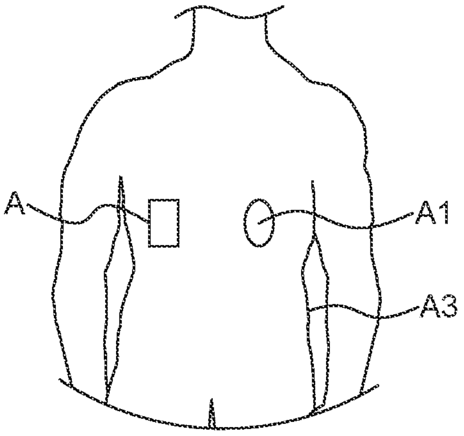
Figure 13B:
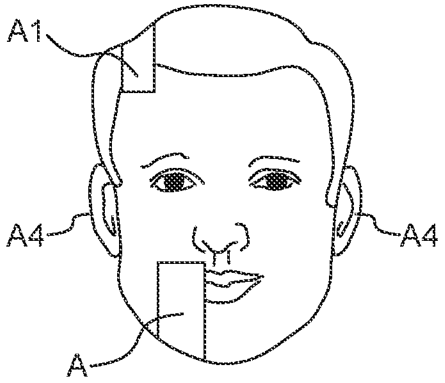
Figure 13C:
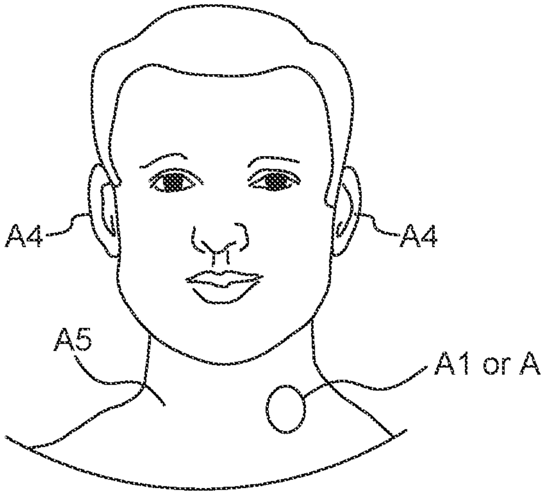
Figure 13D:
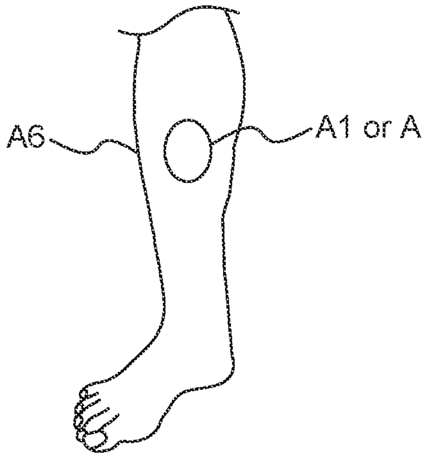
Figure 13E:
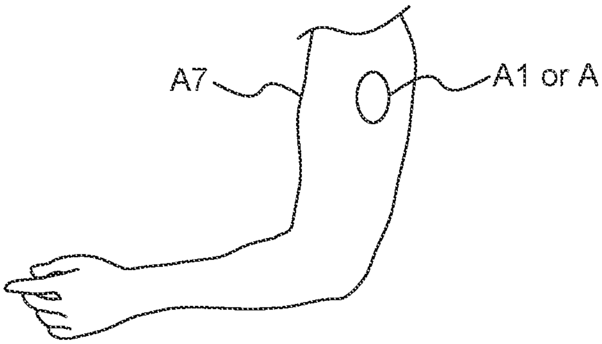
Figure 13F:
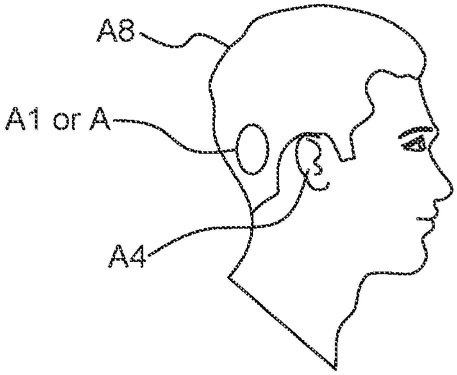
Figure 13G:
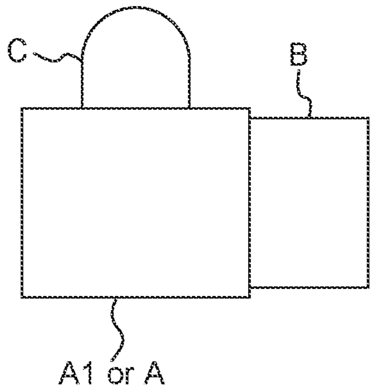

FIG. 13A shows a light source, either a LED array A or a laser diode array A1, worn on a patient's body A3. In FIG. 13B, the light source(s) A and/or A1 is depicted worn near a patient's ear A4. In FIG. 13C, the light source(s) A and/or A1 are shown worn on a patient's neck A5. In FIG. 13D, the light source(s) A and/or A1 are shown worn near a patient's tibial area A6. In FIG. 13E, the light source(s) A and/or A1 are shown worn near a patient's upper arm A7. And in FIG. 13F, light source(s) A and/or A1 are shown worn on a patient's head A8. Further, in FIG. 13G, the light source(s) A and/or A1 may be powered by battery B powered and rechargeable. Also, the light source(s) A and/or A1 may incorporate a controller C which allows for tuning of the emitted light waveband or wavelength, and control of the intensity and light pulse frequency.

Figure 14A:
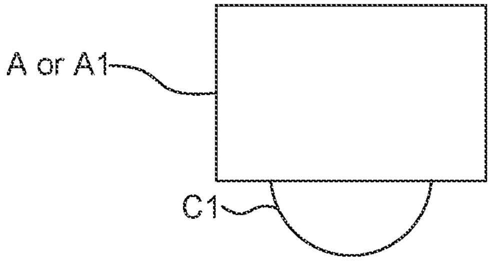
Figure 14B:
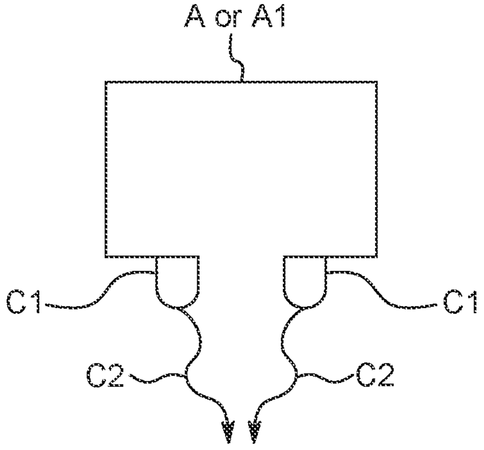
Figure 14C:
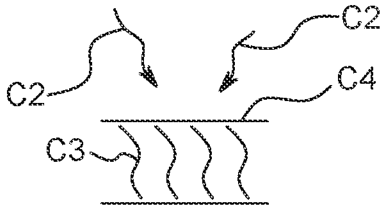
Figure 14D:
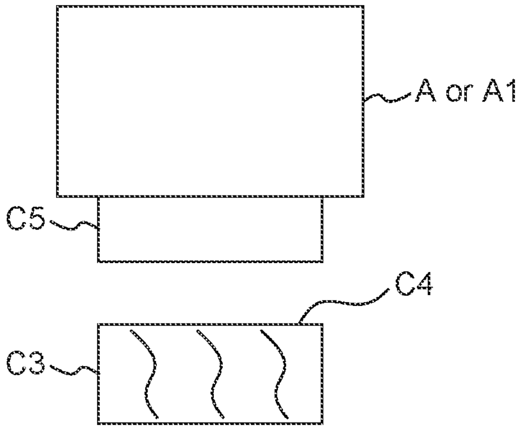

FIG. 14A shows the light source(s) A and/or A1 further incorporating a mechanical aiming mechanism C1 which swivels the light source(s) A and/or Alto enable light beams to be emitted in multiple directions. FIG. 14B depicts the mechanical aiming mechanisms C1 aiming light beams C2 in various directions. FIG. 14C shows light beams C2 being aimed to converge on a target tissue volume C3 and/or surface C4. FIG. 14D depicts light source(s) A and/or A1 array incorporating len(s) C5 to enable aiming and convergence of light beams on a target tissue volume C3 or surface C4.

Figure 15A:
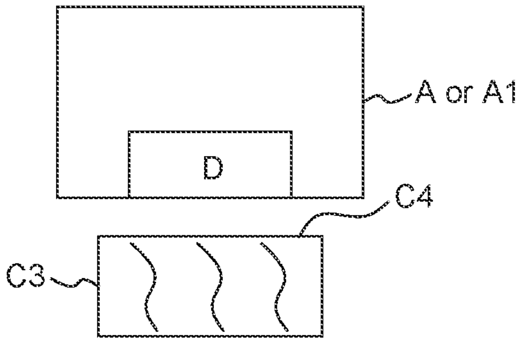
Figure 15B:
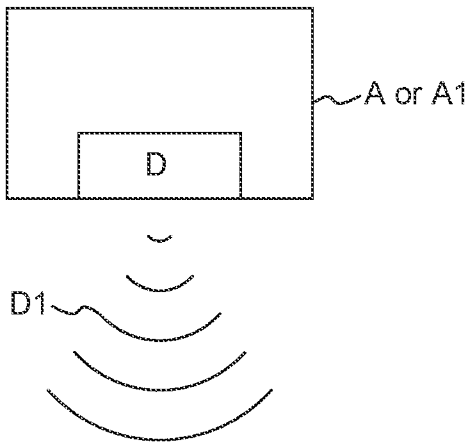
Figure 15C:
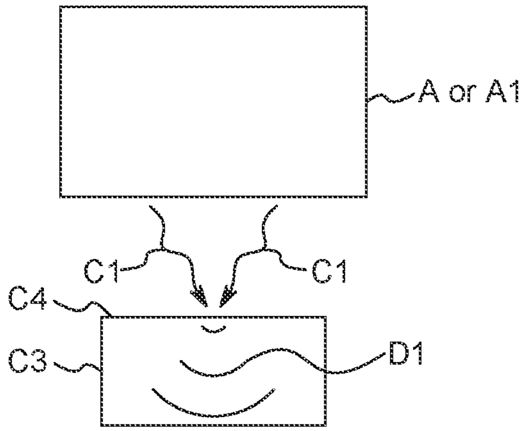
Figure 15D:
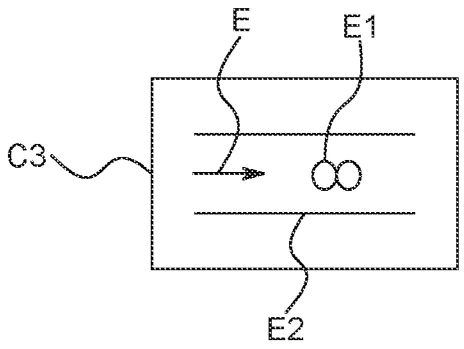
Figure 15E:
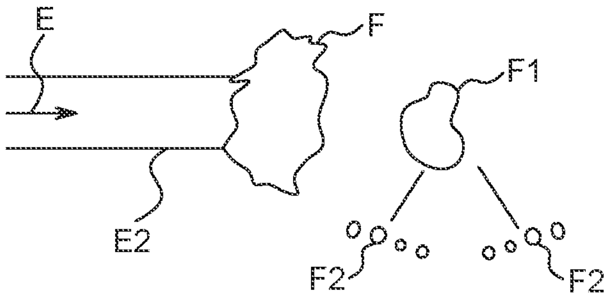
Figure 15F:
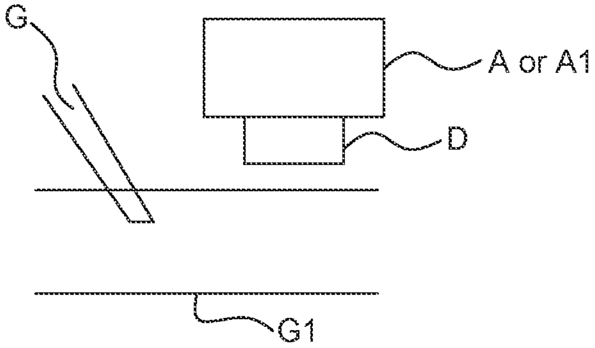

FIG. 15A shows the light source(s) A and/or A1 incorporating ultrasound transducer array D to enable simultaneous delivery of focused light beams to a tissue target volume C3 or surface C4. FIG. 15B shows ultrasound transducer array D generating an acoustic pulse waveform D1. FIG. 15C depicts light beams directed with aiming mechanisms C1 at target surface C4 and the acoustic pulse D1 inducing ischemia in the target tissue volume C3. In FIG. 15D, the induced ischemia in target tissue volume C3 causes a drastic reduction or stopping of blood flow E with a blood clot blockage E1 in blood vessel E2. In FIG. 15E, subsequent recanalization and recovery of blood flow E causes reperfusion in blood vessel E2 depicted by an arrow indicating flow. Further, a large cancerous deposit F supplied by blood vessel E2 is reduced in volume due to an injury reperfusion effect and becomes a smaller cancerous deposit F1 which also releases tumor antigens F2 leading to a beneficial antitumor immune stimulation effect. FIG. 15F shows administration of one or more photosensitizers G into a vein G1, and activation of the photosensitizer(s) by the light source(s) A and/or A1 which incorporates ultrasound transducer array D, where the ultrasound transducer array D is monitoring the overall effect.

Figure 16A:
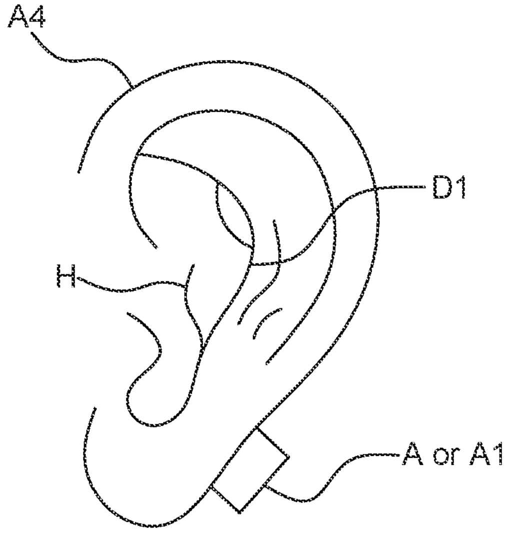
Figure 16B:
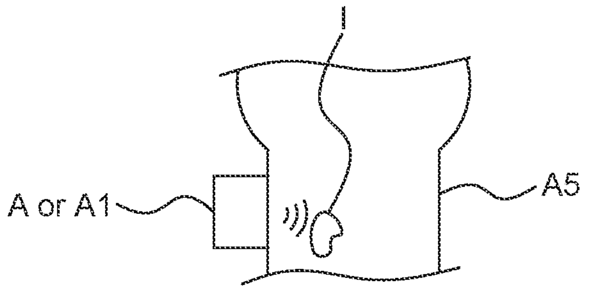
Figure 16C:
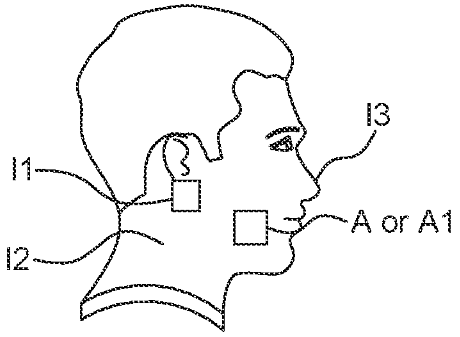
Figure 16D:
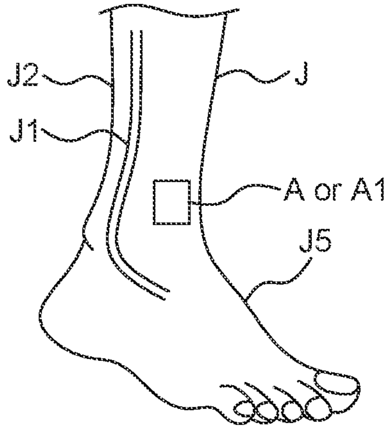
Figure 16E:
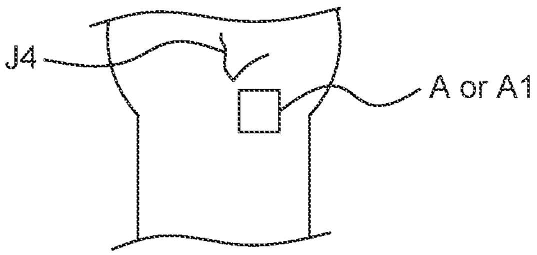
Figure 16F:
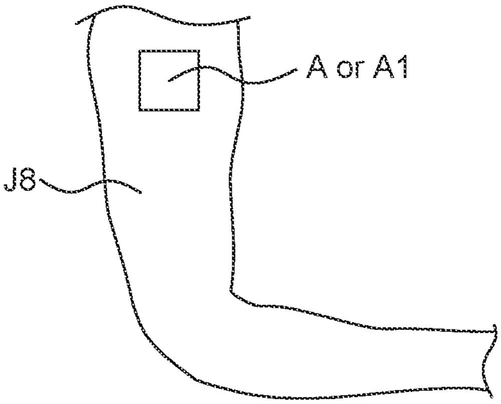
Figure 16G:
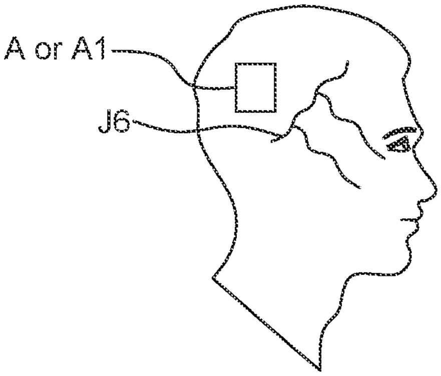
Figure 16H:
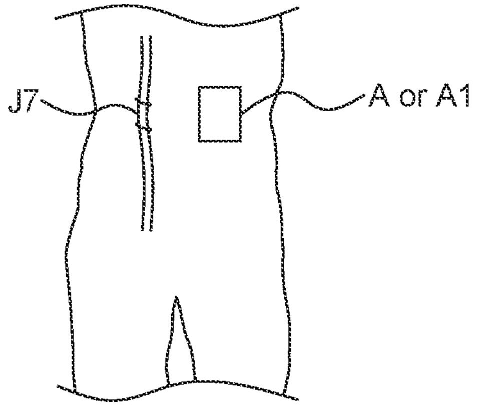

FIG. 16A shows the light source(s) A and/or A1 proximate or reversibly attached to a patient's ear A4, which emit light, generating a series of photoacoustic pulses D1 which stimulate vagal nerve branches H in the ear A4 which may be used to treat various conditions caused by dysautonomia. Similarly, FIG. 16B depicts light source(s) A and/or array A1 proximate or reversibly attached to a patient's neck A5, generating a series of photoacoustic pulses which stimulate the stellate ganglion I and which may be used to treat cardiac and other medical conditions. FIG. 16C shows nasopharynx structure 12 containing sphenopalatine ganglion I1 which is stimulated photo-acoustically by external light source(s) A and/or array A1 lateral to nose 13, which may be used to treat headache conditions. FIG. 16D depicts the tibial area J, specifically the tibial nerve J1 in the lower leg J2 and foot J5, medially, which is stimulated by external light source(s) A and/or A1. FIG. 16E shows light source(s) A and/or A1 providing photo-acoustic therapy to treat an overactive condition for bladder J4. FIG. 16F depicts light source(s) A and/or A1 treating condition in a patient's upper arm region J8. FIG. 16G shows light source(s) A and/or A1 configured to treat a patient's occipital and/or trigeminal nerves J6 for acute and chronic pain, including headache disorders. FIG. 16H depicts light source(s) A and/or A1 positioned externally on the skin a patient's back, proximate to a site of spinal cord injury J7, and configured to induce a photoacoustic effect at the injury location.

Figure 17A:
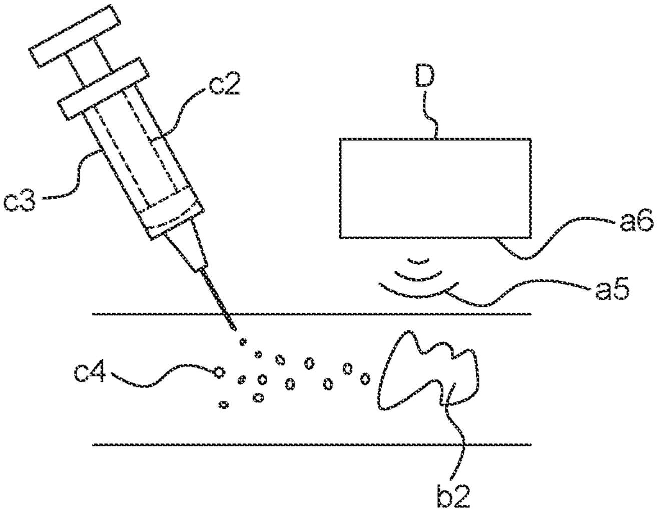
Figure 17B:
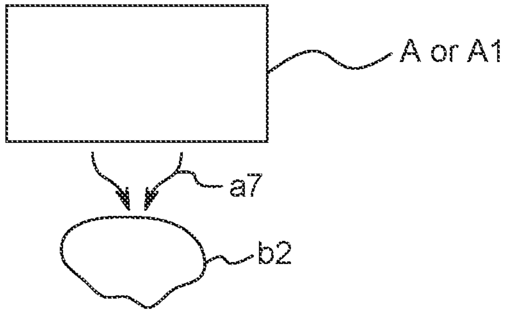
Figure 17C:
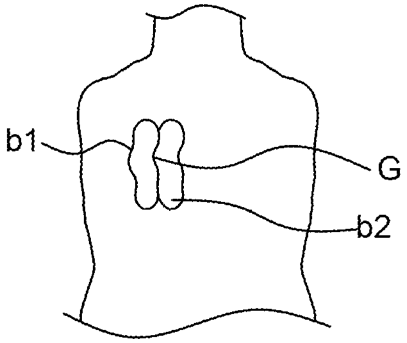

FIG. 17A shows an ultrasound contrast solution c2 in a syringe c3 being injected intravenously c4, and localizing in tumor tissue b2, where external ultrasound transducer D is emitting ultrasound energy a5 and detecting the returning signal a6. FIG. 17B depicts external light source(s) A and/or A1 focusing light beams a7 onto the target tumor tissue b2, which induces the ischemic reperfusion effect referred to in FIGS. 15A through 15F. FIG. 17C shows a patient's thorax with deep lung tissue b1, cancerous deposit b2, and photosensitizer G.

Figure 18A:
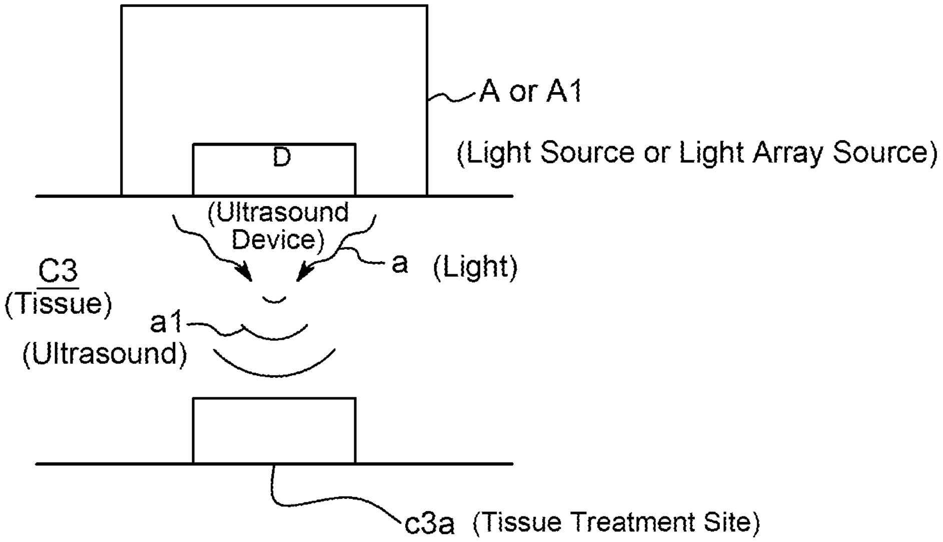
Figure 18B:
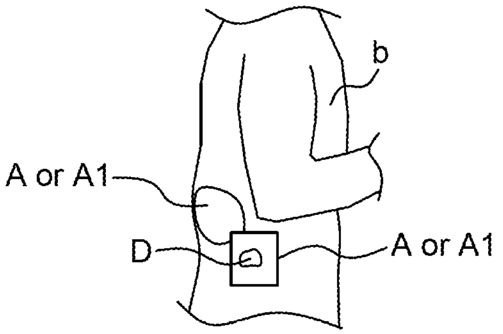

FIG. 18A shows a light source A or A1 array which incorporates ultrasound transducer array D whereby the light source is capable of emitting light at one or more wavelengths and wavebands, enabling specific phototherapeutic treatments and/or photoactivation of at least one photosensitizer formulation, and specific ultrasound generation from the external ultrasound transducer D, which can augment the photoacoustic effect induced by the light source within tissue C3 at different wavelengths and wavebands, for imaging purposes, or for sonodynamic activation, or for enablement of ultrasound specific treatment processes. It is understood that light alone form light source(s) A and/or A1 is also therapeutic. Thus, light source A or A1 can deliver light a, and/or photoacoustic ultrasound al, and/or ultrasound from ultrasound transducer D to treatment site c3*a*, in any combination, sequence, or individually. It is also understood that any of these modalities, external ultrasound, photoacoustic ultrasound, and/or light from light source(s) A and/or A1 can be used to activate at least one photosensitizer. FIG. 18B depicts light source A or A1 array with ultrasound transducer array D positioned on both sides of a patient's thorax b which enables targeting of deep lung tissue b1 where cancerous deposit b2 resides by enabling both light and ultrasound mediated activation of at least one systemically injected photosensitizer c1 which has accumulated in cancerous deposit b2 (See FIG. 17C).

Figure 19:
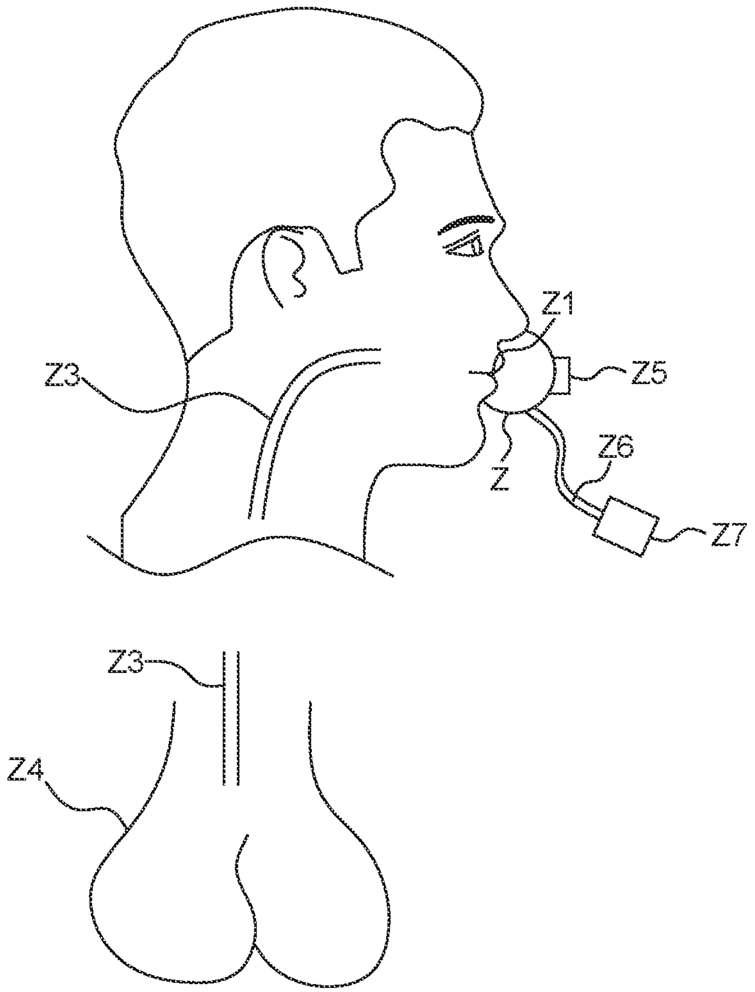

FIG. 19 shows a face mask Z covering mouth Z1 and steam or vapor column Z3 extending through respiratory tract Z4, whereby the steam or vapor column Z3 is transmitting light from light array Z5 incorporated into facemask Z. Steam generator Z7 is shown connected by a flexible tube Z6 connected to facemask Z.

Figure 20A:
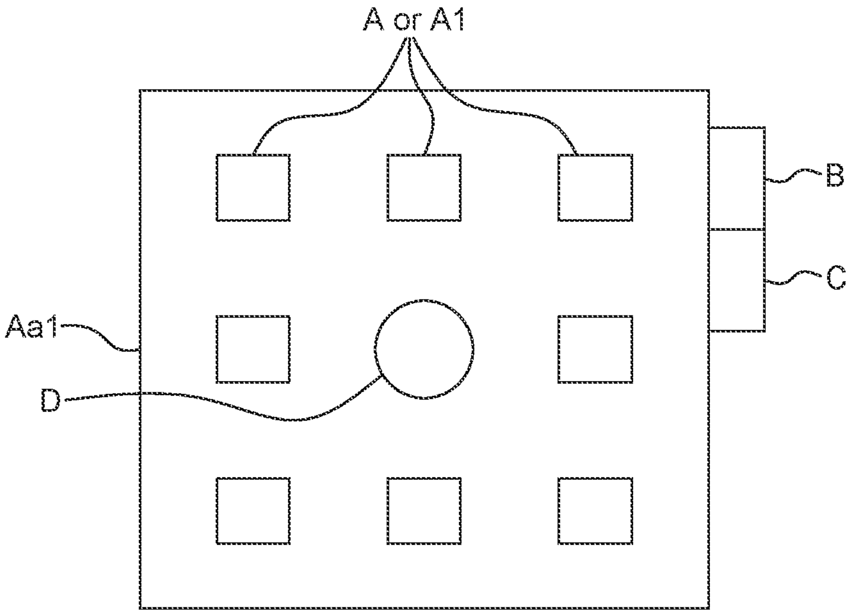
Figure 20B:
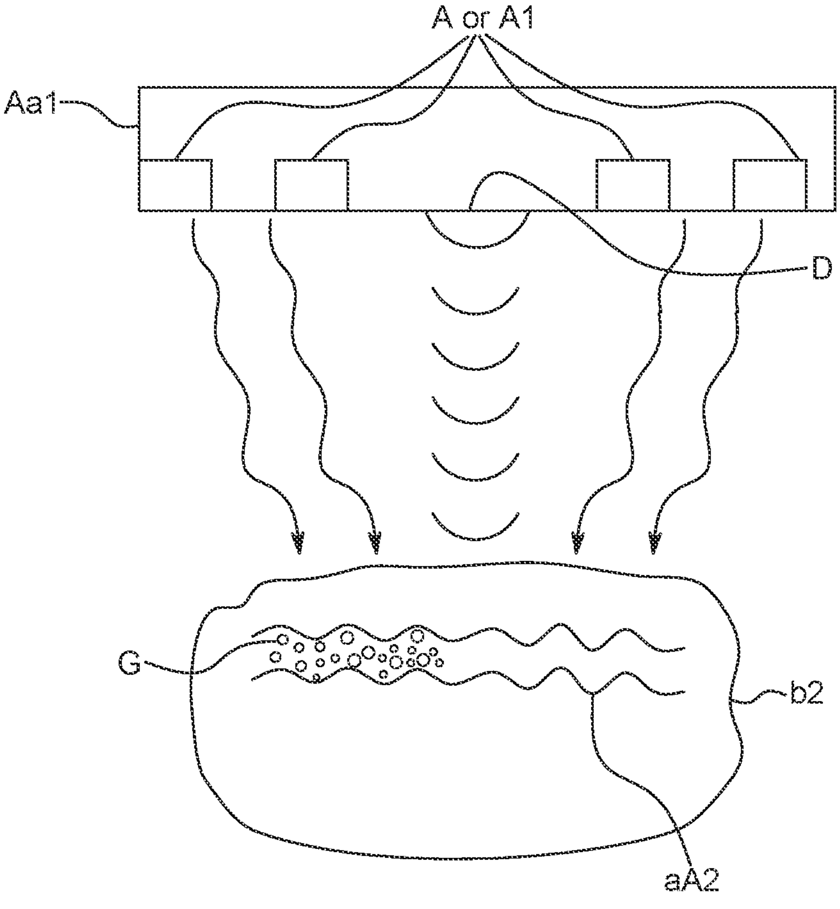

FIG. 20A shows a "top down view" of LED or laser diode array light sources A or A1 located on the perimeter of photoacoustic device Aa1 incorporating battery B and controller C, which is capable of delivering pulsed light to an internal tissue target which may be a pathologic tissue such as tumor tissue b2 (Shown in FIG. 20B), or an atherosclerotic lesion within a blood vessel, or to a nerve such as the vagal which can be stimulated for therapeutic purposes. Such pulsed light can induce a photoacoustic ultrasound pulse at the target tissue site and/or a photoactivation effect on at least one photosensitizer G (Shown in FIG. 20B) and/or a phototherapeutic effect on mitochondria in the absence of an exogenously administered photosensitizer. FIG. 20B depicts a "side view" of device Aa1 with ultrasound transducer D which can be used to image a lesion or target tissue such as a tumor b2, and/or act as another source of externally generated ultrasound energy augmenting the internal tissue photoacoustic effect. For external to internal ultrasound delivered energy and the internal photo-acoustically generated ultrasound pulse, the ultrasound energy serves to activate at least one photosensitizer G sonodynamically, or act in of itself to alter tissue function and/or affect vascular function. For example, closing pathologic tumor blood vessels aA2. The same or somewhat similar modalities may be used for tissue imaging, and imaging of the therapeutic effect evidenced by detection of tissue changes and vascular flow changes as can be ascertained using color flow and power doppler measurement techniques.

DETAILED DESCRIPTION OF PREFERRED EMBODIMENTS

Figure 1:
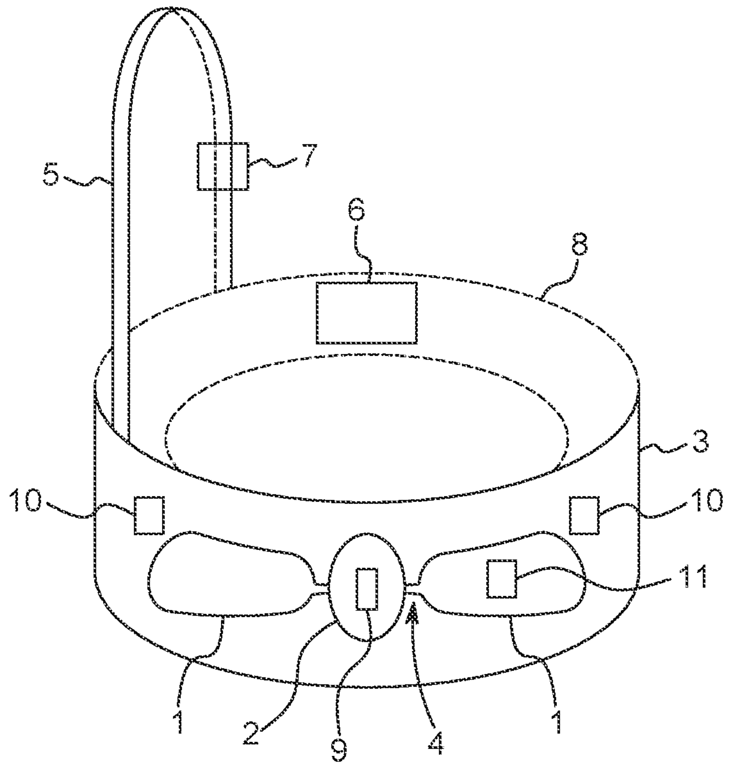
FIG. 1 is a schematic drawing of a belt worn around the abdomen which incorporates two compressed gas cylinders connected by a tubes to an inflatable bag.

The embodiment in FIG. 1 is a belt or band 3 comprised of a flexible but non-elastic breathable polymeric material such as a nylon band worn around the abdominal region which incorporates at least one compressed gas cylinder 1 used for inflation, connected by a tube 4 to an inflatable elastomeric bag, bladder, or balloon 2, which remains in the collapsed state prior to inflation device activation. When the inflatable bag, bladder, or balloon 2 which is comprised of polymeric, elastomeric material such as the nylon compositions commonly used in vehicular airbags, is rapidly filled with compressed gas, pressure is exerted which compresses the anterior abdominal wall, transiently raising the intra-abdominal pressure. In all embodiments and constructs utilizing inflatable bags, bladders, or balloons 2, the constructs dimensions are such that safe bodily compression is enabled by limiting the expansion of the construct. In other words, the process of fabrication and manufacturing of the inflatable articles 2 determines the shape and volume of 2 when fully inflated. In yet another embodiment, the belt or band 3 may be flexible anteriorly and incorporate a rigid conformable section 8 posteriorly which may be comprised of a lightweight polymeric substance which facilitates the effective application of pressure by the expanded bag, balloon, or bladder 2 to the anterior or anterolateral abdominal wall. The compressed gas cylinder 1 also incorporates a means of on demand rapid gas release, for example using a valve apparatus 11 which rapidly opens just prior to an impending collision, impact, blast force, or other potentially injurious event. The belt or band 3 diameter is adjustable using a buckle, clasp or fastener 6 which is incorporated into the belt or band 3. The belt or band 3 also optionally incorporates a suspender 5 which is adjustable using buckle 7. The belt or band 3 also optionally incorporates a pressure sensor 9 which abuts and detects the pressure applied to the anterior abdominal wall. Pressure sensor 9 serves to indicate the correct tightness and fit of the belt or band 3, and can also indicate and regulate the correct degree of compression that occurs with compression device activation. Pressure sensor 9 prevents inadvertent excessive compression force which could harm the abdomen, thorax, or pelvis. The belt or band 3 also optionally incorporates at least one collision, impact, or motion detector 10 which can utilize ultrasound, infrared, electromagnetic sensing, and/or an accelerometer and/or gyroscope, and/or pressure sensor or GPS device, which senses the potentially injurious event and activates the abdominal compression device just prior to the impending event causing pathologic brain movement, and/or pathologic force application to the brain. The abdominal compression component 2, which is a balloon, bag, or bladder, is comprised of an expandable polymeric substance, which is inflated to a fixed pressure by at least one compressed gas cylinder 1. The abdominal compression component 2 can compress the abdomen or pelvis, or both, by varying the size of its construction, or by varying the inflation pressure from the gas cylinder 1. A propellant is also utilized in another embodiment and contained either in cylinder 1 or in collapsed bag, bladder, or balloon 2 and is activated on demand to prevent or reduce brain jury, by the collision and impact apparatus 10.

Figure 2:
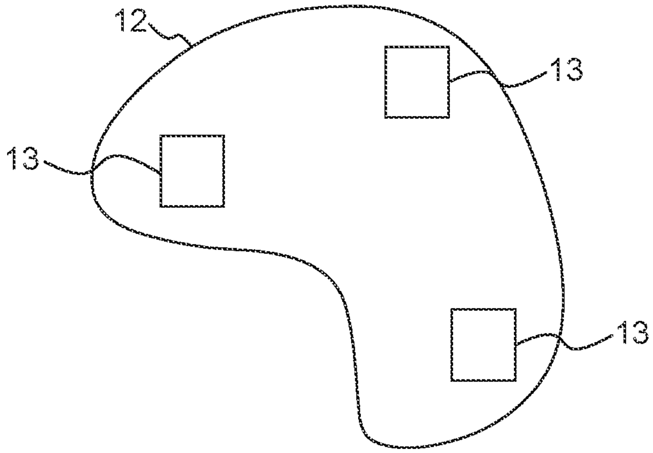
FIG. 2 is a schematic drawing of a helmet which incorporates impact and collision sensors which are connected wirelessly or by a wired connection to the abdominal compression device.

Another embodiment is shown schematically in FIG. 2 and which also optionally utilizes an impending collision, impact, or abnormal head movement detection system and apparatus with a battery power source and transmitter 13 which is mounted on, or incorporated into a helmet 12. The battery in component 13 is disposable or rechargeable. The transmitter in 13 is connected by wires or is wirelessly linked to the abdominal and optional pelvic compression component 2 and activates the compression mechanism just prior to the potentially injurious event. In another embodiment the collision, impact, or harmful head movement detection system and apparatus 13 is incorporated remote to the user, for example in a bicycle, a vehicle, or other conveyance. The impending injury detection and apparatus 10 (FIG. 1) and 13 optionally uses at least one ultrasound transducer, and/or at least one infrared or pyroelectric sensor (Kim 2015), and/or at least one electromagnetic high frequency microwave sensor component, and/or at least one radar device, and/or at least one accelerometer, gyroscopic device, pressure sensor, and/or GPS device to detect an impending collision, impact, sudden head acceleration or deceleration, blast force, or other sudden head motion which could adversely affect the cerebrum.

Figure 3:
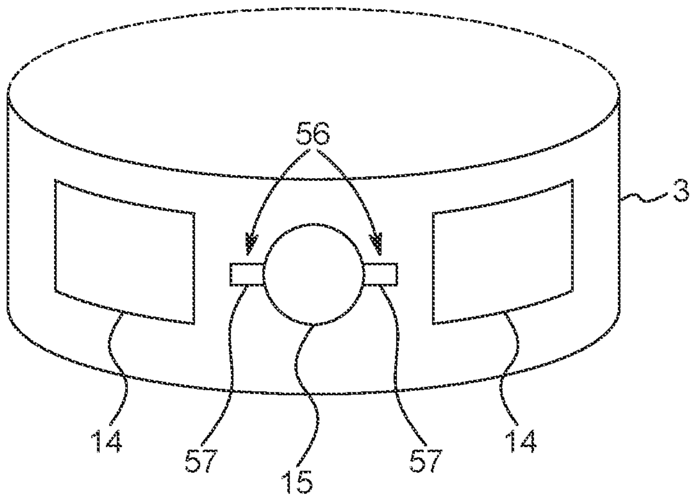
FIG. 3 is a schematic drawing of a belt worn around the abdomen which incorporates an anterior abdominal, pelvic, or thoracic compression device component which uses a winding mechanism driven by a rotating motor to exert pressure against the abdomen, pelvis, or thorax.

The embodiment depicted schematically in FIG. 3 is a belt or a band 3 which incorporates a compression construct 14 which is a rigid or semi-rigid polymeric plate, fitted or molded to conform to the anterior or anterolateral body wall, positioned against the body wall, which also incorporates an expandable member comprised of a bag, balloon, or bladder. Expanding the bag, balloon, or bladder results in compression of the body wall by the plate, followed by decompression of the body wall as the bag, balloon, or bladder deflate by way of vent holes or a venting valve. Also shown is a winding mechanism comprised of a high rotational speed battery powered, bi-directional motor 15 controlled by a CPU, which activates the motor prior to an impending harmful event. Activation of the motor causes it to wind around one axis direction for torso or pelvic compression, followed by an unwinding motion in the opposite axis direction resulting in torso and pelvic decompression. The winding mechanism further is comprised of at least two straps 56 positioned around the motor 15, which extend laterally to the motor, which are also attached to the belt or band. When the motor rotates in one axis direction, the straps 56 whose distal ends 57 are glued or sewn to the belt or band, wind around the motor mechanism proximally to tighten the belt or band, and unwind by way of motor rotation in the opposite axis direction. The winding mechanism tightens the belt or band 3 transiently by pulling the lateral segments of the belt or band together upon activation, prior to a potentially injurious event, resulting in body wall compression. Activation of either mechanism shown in FIG. 3 exerts pressure on the anterior abdominal wall, anterior torso, or pelvis, which transiently compresses the body cavity. The compression construct and mechanism 14 is normally in the compressed or collapsed state and is activated just prior to a potentially injurious event. The winding mechanism and motor 15 releases the belt or band tension rapidly after activation by counter rotation which can be induced by the CPU, which switches the motor rotation direction.

Figure 4:
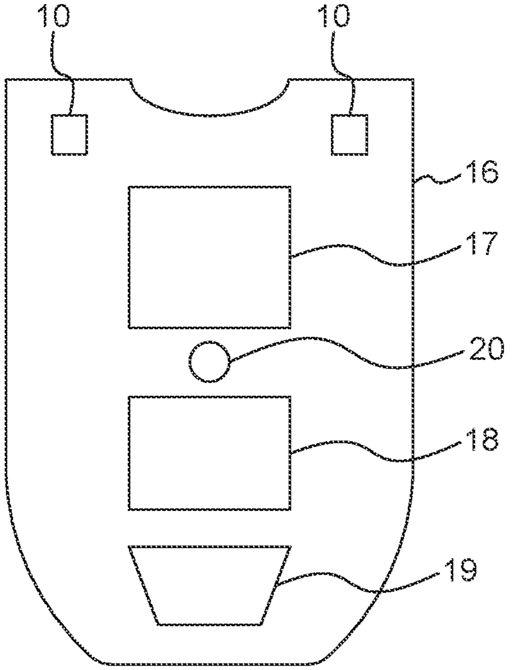
FIG. 4 is a schematic drawing of a vest-like garment showing the anterior aspect, which incorporates thoracic, abdominal, and pelvic compression devices, with an incorporated CPU controller.

The embodiment depicted schematically in FIG. 4 is a vest-like garment 16 which incorporates block diagrams of a thoracic compression device 17 which is positioned over the sternum, and when activated depresses the sternum to a predetermined depth between 1 cm and 8 cm, an abdominal compression device 18, which can be comprised of one, or multiple separate compression devices which can compress the abdomen in the midline, or on either side of the midline anterolaterally, a pelvic compression device 19, and a controlling CPU 20 which activates the compression devices sequentially from a caudal to a cephalad direction, or the pelvic 19 and abdominal 18 compression devices simultaneously, followed by the thoracic compression device 17, or the pelvic 19, abdominal 18, and thoracic 17 compression devices simultaneously. The CPU 20 is pre-programmed to work in concert with impact, collision, or blast detection system and apparatus 10 and 13, whereby the impending potentially injurious event is detected and the protective devices 17, 18, 19, activated by the CPU 20. The CPU 20 can receive the impending injury event data, predict the severity of the impending harmful event, and deploy the compression devices accordingly such that the degree, rate, depth, duration, and location of compression corresponds to the optimal protective degree of cerebrospinal fluid displacement, brain stiffening and brain tissue compliance reduction. Thus, compression parameters are optimized to prevent excessive compression, or inadequate compression by devices 17, 18, or 19 upon activation by CPU 20. The array of pressure sensors, and impending impact sensors which may utilize ultrasound, infrared light, or be electromagnetic, and/or at least one or an array of accelerometers and/or gyroscopes, and/or GPS locating devices, which communicate to the CPU 20 are represented by block diagrams 10.

Figure 5A:
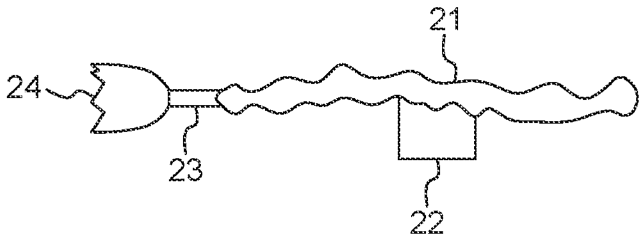
FIG. 5A is a schematic drawing of a collapsed air bag comprised of an expandable, elastomeric material.
Figure 5B:
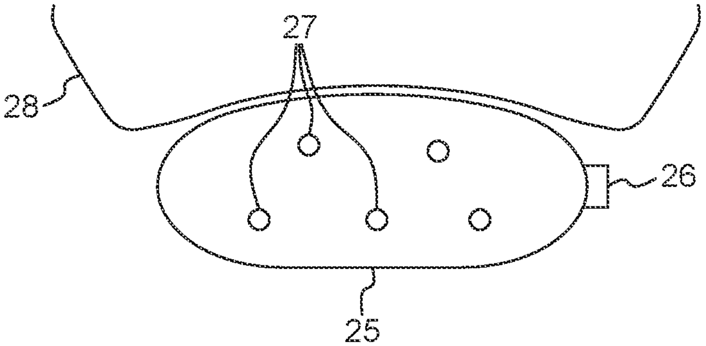
FIG. 5B is a schematic drawing of the air bag when inflated either by compressed gas or propellant compresses the anterior torso body wall.

The embodiment depicted schematically in FIG. 5A is a collapsed airbag 21, bladder 21, or balloon 21 which is inflated by compressed inert gas contained in a cut-away view of metallic or polymeric cylinder 24. The embodiment shown schematically in FIG. 5B depicts when a gas has been released from a container by a valve incorporated into cylinder 24 is conveyed by tube 23 to the expandable structure 21. The expanded airbag 25, bladder 25, or balloon 25 also incorporates a gas escape valve 26 and/or vent holes 27 which permit gas to escape after inflation of structure 21. The anterior body wall 28 can be the pelvis and/or abdomen and/or thorax, and is shown in a compressed mode which forces cerebrospinal fluid from the spinal dural sac towards the intracranial compartment which reduces or precludes harmful brain movement, while also increasing protective brain stiffness by way of reduced venous return towards the thorax from the intracranial venous system.

Figure 6A:
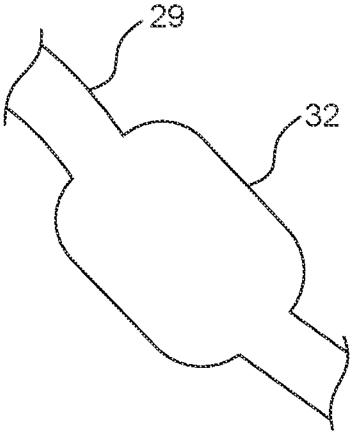
FIG. 6B is a schematic drawing of a lap belt and FIG. 6A is a schematic diagram of a shoulder belt incorporating compression devices for use in a vehicle such as an automobile, truck, or any other conveyance where belted restraints are used.
Figure 6B:
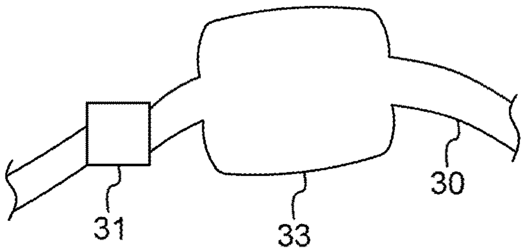

The embodiment shown schematically in FIG. 6B is a seat belt restraint 30 in a cut-away view with an adjustable buckle 31 which incorporates an abdominal compression device 33; and the embodiment depicted schematically in FIG. 6A is a shoulder belt restraint 29 in a cut-away view which incorporates a thoracic compression device 32.

Figure 7:
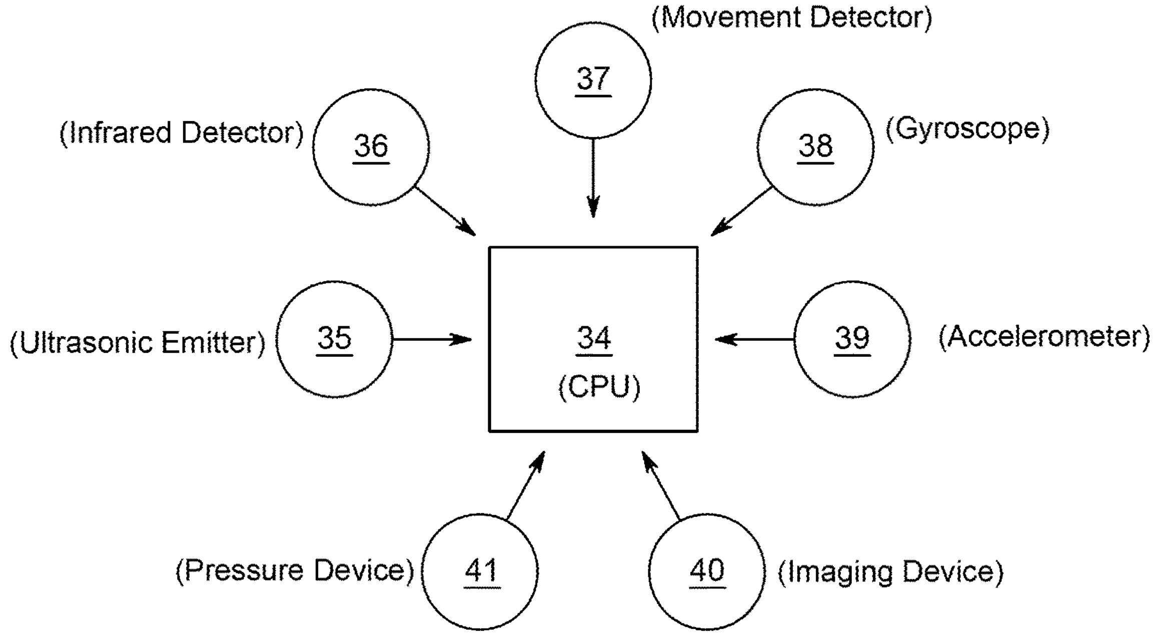
FIG. 7 is a schematic drawing of a CPU which receives input from collision, impact, and motion detectors collectively known as the sensing devices. The CPU serves to integrate the warning data from the sensing devices to activate the compression devices at the appropriate time to provide brain protection.

The embodiment depicted in FIG. 7 is a CPU 34 which receives input represented by the straight arrows from various impending injury sensing devices which can constitute an array, including at least one of an ultrasonic emitter and detector 35, an infrared movement detector 36, an electromagnetic movement detector including radar or lidar 37, a gyroscopic position detector 38, an accelerometer 39, a machine vision and imaging device 40, and a pressure sensing device 41. The CPU and/or the sensing devices can be optionally incorporated into a helmet, headband, garment, belt, harness, body armor, cycle, vehicle or other conveyance used for user transport, or deployed in the environment around the user, for example using a drone. The CPU 34 optionally contains preloaded information, algorithms, and data relating to crashes, collisions, user motion, and impacts, and receives and integrates real-time data and information from the sensing devices to activate the compression devices just prior to abnormal, pathologic, and potentially injurious brain movement or deformation.

Figure 8:
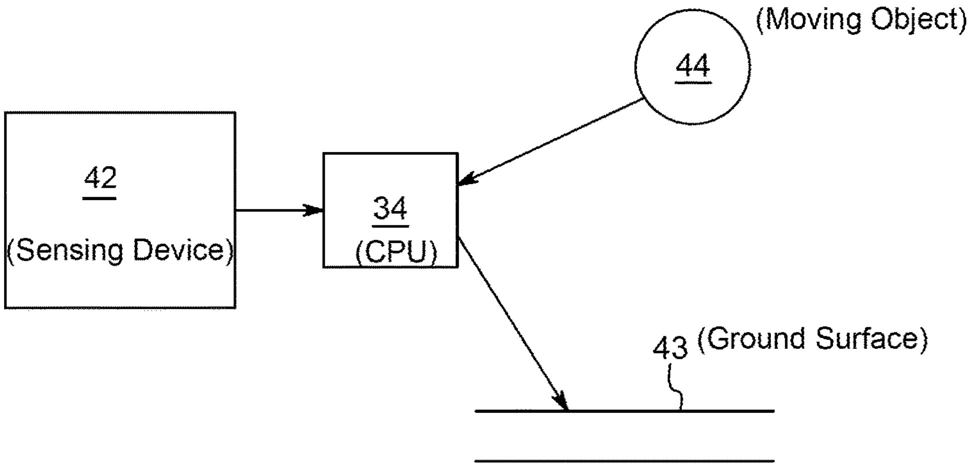
FIG. 8 is a schematic drawing of an impending ground collision or impact from an object in the user's environment that is detected by a sensing array which communicates the data to a CPU.

The embodiment depicted schematically in FIG. 8 shows a block diagram of the sensing device array 42 which is worn by the user or is separate from the user. The sensing device array 42 signals the CPU 34 that the user is about to collide with the ground or a surface 43, the impending collision represented by the straight arrow aiming at ground or surface 43 or be impacted by an object in the immediate environment 44, the impending impact by object 44 represented by the straight arrow aiming at the CPU 34. The CPU 34 activates the compression device or devices just prior to the injurious event which prevents or reduces brain injury. Both the sensing device array 42 and the CPU 34 capable of recording, receiving, and sending collision and impact data. The sensing device array 42 can also optionally incorporate a pressure sensor which can record aspects of impact or collision data such as speed, force, direction, and duration in the event of an impact or collision.

Figure 9:
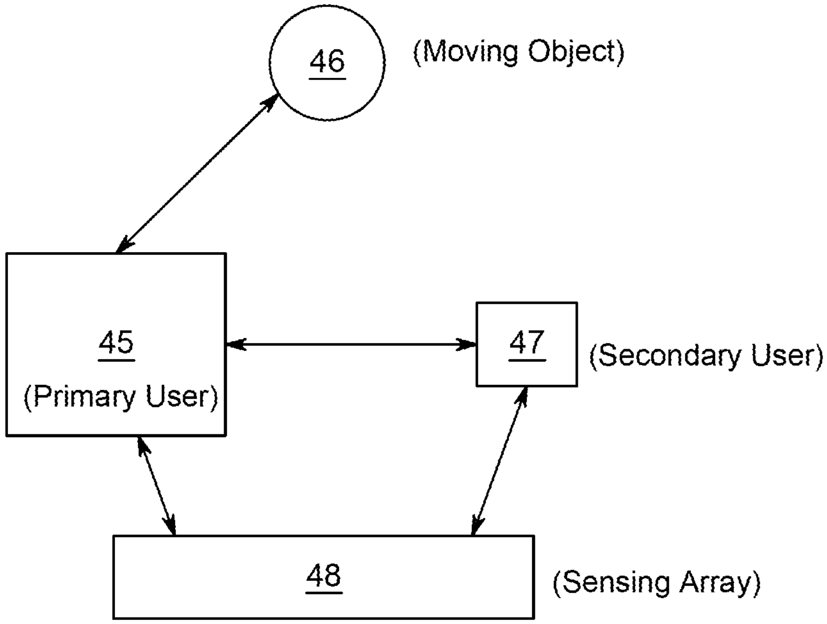
FIG. 9 is a schematic drawing of a two-way communication system between the user and an object or another individual in the user's immediate environment whose impending impact or collision interaction with the user enables appropriate activation of the compression device, to protect the user's brain.

The embodiment shown schematically in FIG. 9 represents a schematic block diagram of primary user 45 wearing sensing array/CPU 34 (not shown) in receiving data from moving object 46 which could be a soccer ball for example, incorporating a sensing array which is transmitting impending impact and collision data to user 45 to determine the need for a compression device to be activated such as schematically depicted in FIGS. 1, 3, and 4. Primary user 45 may also be receiving and transmitting collision and impact data to secondary individual user 47 who is also equipped with a sensing array/CPU 34, which determines the need for activation of the compressive devices of FIGS. 1, 3, and 4. Also shown in block form is at least one sensing array 48, in a stationary location, for example of a sports playing field which relays and receives impending impact and collision data from primary user 45 and 47. In all cases the CPU 34 can carry out at a minimum, two-way communication as schematically depicted in FIG. 9 which enables data collection and analysis of impacts, collisions, head movements and the like, which can be further analyzed and corroborated with outcomes and sequelae to improve overall function and efficacy of the one or more of the various embodiments.

Figure 10:
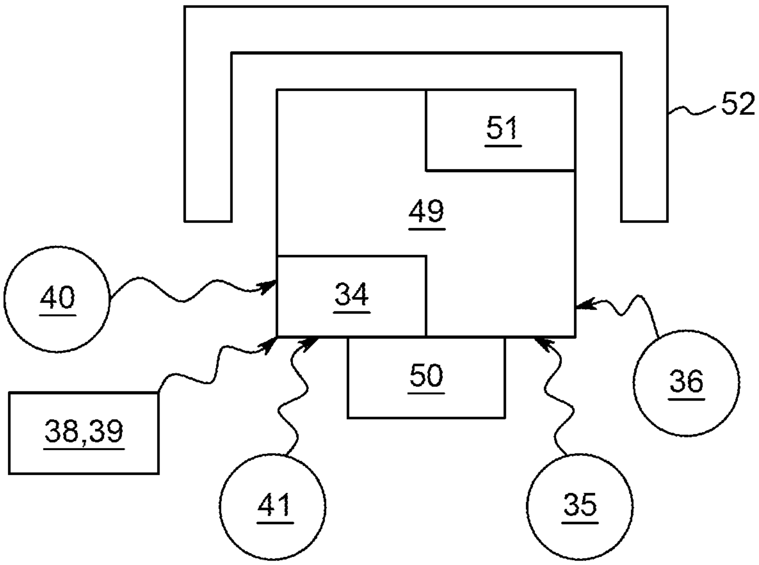
FIG. 10 is a schematic drawing of a small, compact, self contained sensing array also incorporating a battery and a CPU, which can be positioned and optionally repositioned on a user's body, conveyance, or on or within an object in the user's environment, as needed.

The embodiment depicted schematically in FIG. 10 is a block diagram schematic showing a self contained sensing array 49 which is compact, lightweight, which incorporates a battery power supply 51 and can be securely positioned or moved and repositioned to a different location on the user's body, or on a conveyance or vehicle such as a bicycle, motorcycle, or automobile, or on a helmet or garment worn by the user, or on a seat belt, or on an object in the immediate environment of the user such as a ball, using a fastener or fastening system 50 which may be comprised singly or of a combination of a strap, lacing, Velcro hook and loop binding, clamp, threaded screw, socket, tape or other sticky film, or which can be reversibly inserted into a housing 52 designed specifically to contain the sensing array 49 which is incorporated into a garment worn by the user, a conveyance employed by the user, and/or an object in the user's environment which interacts in some with the user. Sensing array 49 incorporates at least one of an infrared sensor 36, an ultrasound sensor 35, a pressure sensor 41, a gyroscopic position detector 38, an accelerometer 39, a machine vision and imaging device 40, and/or any combination of the sensing array components and devices including the CPU 34 depicted in FIG. 7. The self contained sensing array 49 may be configured to activate the compression device embodiments as schematically depicted in FIGS. 1, 3, 4, 5, and 6.

Figure 11:
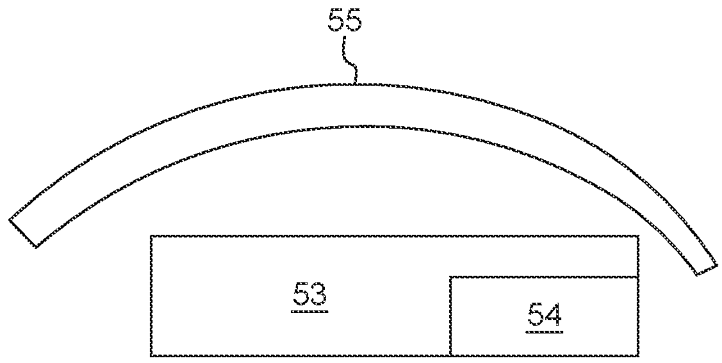
FIG. 11 is a schematic drawing of a low profile, compact compression or ultrasound/photoacoustic device for military or recreational or professional sports use.

The embodiment schematically depicted in FIG. 11 is a schematic block diagram showing a compact compression device 53 which is low profile and incorporates the compressed gas container and/or propellant substance 54 within its confines. The compression device 53 is optionally covered and protected from direct impact damage by a covering 55 optionally comprised of cloth or foam padding, bubble wrap insulation, or other energy dissipating, compressible materials and substances, or rigid shielding material such as ballistic resistant armor or polymers and plastics used for helmet construction for example.

Figure 12:
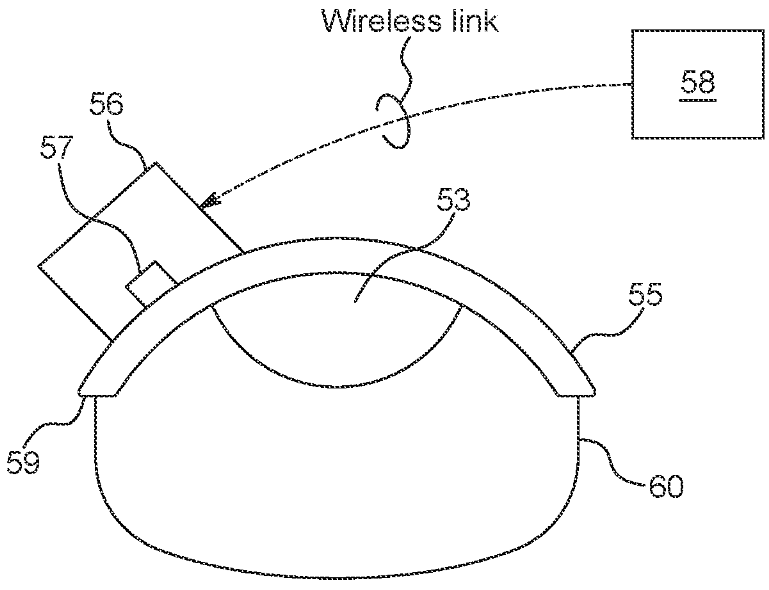
FIG. 12 is a schematic drawing of a suction device, activated by detection of a blast wave, which serves to mitigate against harmful increases in intracranial pressure due to the initial overpressure wave of the blast.

The embodiment schematically depicted in FIG. 12 represents a schematic block diagram depicting the suction device or ultrasound or photoacoustic device 55 which is positioned anteriorly, or anterolaterally on the abdomen and optionally on the pelvis as well. The suction or ultrasound or photoacoustic device 55 is comprised of a polymeric or metallic material that is rigid or semi-rigid, and is optionally incorporated into military style body armor, such that the interior of suction or ultrasound or photoacoustic device 55 faces the abdominal and pelvic wall anteriorly. The general shape is that of a circular or oblong dome, whose rim 59 is shaped to conform to the abdominal and optionally the pelvic wall, anteriorly, or anterolaterally. The rim 59 may incorporate a biocompatible temporary adhesive, such as those used by patients wearing colostomy and ostomy appliances and bags, which may be manually applied as a liquid, paste, cement, powder, tape, or a spray, which allows suction device or ultrasound/photoacoustic device 55 to adhere to the skin surface, forming an airtight and sweat proof seal. Alternatively, a separately applied, double sided adhesive such as that used to adhere colostomy bags to the abdomen is utilized. In addition, another embodiment utilizes a strap, band, or harness 60 that helps to hold suction device or ultrasound or photoacoustic device 55 in its proper place and orientation. The suction apparatus or device or ultrasound/photoacoustic device 55 incorporates a vacuum canister or container 56 which also incorporates a valve 57 which is actuated by the detection of the impending arrival of a blast wave, by a pressure sensor 58 which is separate from the user. Suction or ultrasound or photoacoustic device 55 may optionally incorporate a venturi type vacuum pump, powered by compressed air from a compressed gas cylinder or container. The pressure sensor 58 detects the blast wave, and communicates wirelessly with the suction or ultrasound or photoacoustic device 55, to activate the device 55, just prior to the arrival of the blast wave. The suction device activation leads to generation of a vacuum or pressure reduction within the hollow section of the suction device 55 facing the skin surface, which decompresses the abdomen and optionally the pelvis for a very brief time period, between 1 ms to 1 sec. The vacuum is generated by actuation and opening of a valve 57 located between vacuum cylinder or container 56. This decompression event causes the intracranial pressure to be lowered transiently, reducing or preventing brain injury by compensating for the uncontrolled, dramatic, sudden harmful and injurious increased intracranial pressure from the initial overpressure wave of the blast. The suction device 55 is activated by rapid opening of a valve 57, which may utilize a solenoid type of mechanism, which opens the connection between the vacuum canister or container 56, allowing air entrapped within the dome which is sealed to the skin, of suction device 55, to rush into the vacuum chamber of cylinder or container 56. Element 56 can also represent an ultrahigh speed pump that rapidly evacuates air within the suction device interior. This action creates a transient low pressure zone within the suction device dome, between −5 mm Hg to −75 mm Hg, which displaces the abdomen and optionally the pelvis anteriorly towards the inner surface of the suction device 55. This action transiently reduces intraabdominal pressure which causes cerebrospinal fluid within the dural sac to shift from a cephalad to a caudad direction, which in turn reduces intracranial pressure transiently, for the duration of the overpressure component of the blast wave. In addition, venous return from the brain may be enhanced, which further mitigates against a harmful intracranial pressure rise from the blast wave, by increasing brain compliance. A secondary valve 58 or the two port solenoid 57 rapidly and completely releases the vacuum after the pressure wave of the blast passes, which then allows for the compressive device 59, also incorporated into the suction device or ultrasound or photoacoustic device 55, to be secondarily activated, which mitigates secondary brain impact and/or deformation by The compression device 59 purpose, design, engineering, components, and function is identical or similar to that previously described for compression device 53 and is activated to mitigate brain injury as described in previous sections. The suction device 55 may incorporate one or more vacuum cylinders, canisters, or containers 56 and the functionality, shape, volume, and configuration of suction device or ultrasound or photoacoustic device 55 is determined by way of preclinical, clinical testing, and imaging, as is useful for design and construction of compression device 59.

The following examples listed below are intended to be exemplifications of the one or more of the various embodiments and are not intended to be limiting in any manner.

Example 1

Optimization of the one or more of the various embodiments by design, function, operation, other characteristics, and device compression parameters that enable brain protection against trauma is enabled by use of noninvasive MRI imaging and analysis of cerebrospinal fluid movement, brain movement, brain deformation, and MRI elastography determined brain stiffness caused by device induced compression of the pelvis, and/or abdomen, and/or thorax (Bayly 2005, Feng 2010, Hiscox 2016). Graded, controlled compression of the pelvis, abdomen, and thorax using various weights (Citerio 2001, Koral 2010), or other pressure applying mechanical apparatuses of various size and dimensions is used to cause and determine the optimal degree, rate, and volume of cerebrospinal fluid movement and the degree, and time course of brain stiffening which will provide optimal brain protection, when the head and body are in varying positions, anticipating various scenarios and situations.

In addition, the optimal anterolateral torso and pelvic location, direction, volume, and surface area of compression can be determined based on experimentally optimized cerebrospinal fluid movement and brain stiffening determinations. Also, the optimal sequence of compression, which may for example start in the pelvic region and progress in a cephalad direction can be determined. One or more of the various embodiments may also anticipate that different individual users with different anatomical characteristics and who are likely to experience different probable impact, collision, and head movement events will require different compression parameters to optimize brain protection. In general, the least amount and degree of compression that accomplishes the desired cerebrospinal fluid movement and reduction in brain compliance can be ascertained using MRI and other related or similar tests. In a similar fashion, controlled safe experimental head movement in human volunteers which simulates collision and impact scenarios with the head in flexion, /or extension, and/or rotation is evaluated with MRI imaging and elastography can be used to determine optimal compression parameters (Bayly 2005, Hiscox 2016, Ji 2004, Zhu 2003) to prevent or minimize abnormal, harmful brain movement and brain tissue deformation. Device compression parameters are optimized by including testing variables such as torso pressure onset timing, rate of compression increase and decrease, duration of peak pressure, and the torso volume, area, and location of compression that lead to and correlate with optimal protective timing, duration, and degree of cerebrospinal fluid displacement, along with optimal brain stiffening parameters. All of this data is used to determine the compression parameters that optimize brain protection, and to insure protection of the torso and pelvis against excessive compressive force which could cause inadvertent injury.

Example 2

The belt, abdominal binder, corset, or thoracic located compressor can be adjusted to fit the user utilizing various buckles, a Velcro fastener, or lacing, or other types of fasteners and clasping mechanisms or be pre-fitted to the user. Adjustable shoulder straps and/or leg loops that help to secure the compression apparatus to the correct position on the torso are also an optional feature of the one or more of the various embodiments. The compression device can also be incorporated into clothing in contact with the abdominal, pelvic, and/or thoracic area, or as a component of body armor.

Example 3

The impending injury sensing device array which is comprised of at least one pressure sensor, and/or accelerometer, and/or gyroscope, and/or ultrasound, infrared, electromagnetic, machine vision/imaging apparatus, radar, lidar, and the like are used to detect and assess the motion of the user's head and the likelihood of an impact, collision, blow, or other harmful head motion such as a whiplash type of movement. In addition, the sensing device array may sense an impending collision with a stationary or moving object in the environment around the user which poses a threat which is evaluated by the CPU, which in turn activates the compression device appropriately to negate or reduce brain injury. The sensing device array is worn by the user, and/or incorporated into a conveyance utilized by the user. The sensing device array enables the CPU to calculate time to impact, collision, and/or abnormal brain movement by sensing user head/body motion and/or movement of objects toward the user which can result in brain injuries. This warning capability optimizes the timing of the compression device activation. The compression device component is activated prior to the likely harmful event to reduce injurious brain movement and deformation.

Example 4

In one embodiment at least one pressure sensor and regulator is incorporated into the compression device or is disposed separately from the compression device, which informs the user and allows the user to adjust the tightness, tension, snugness, and fit of the compression device over the abdomen, and optionally the pelvis and thorax. At least one of the same or a separate pressure sensor aids in regulation of the predetermined compression device parameters in terms of the speed, degree, and depth of compression, and optionally which part of the user's body is compressed and in what sequence, by a compression device segmented to allow for separate compression of the abdomen, pelvis, and thorax.

Example 5

Head and brain injuries are an ever present threat to bicycle riders, skate board riders, those who engage in winter sports such as skiing and snowboard riding, ice skaters, roller skaters, and other individuals engaging in similar activities, where collisions with the ground can occur. Although a substantial number of these individuals may wear a helmet, it is widely acknowledged by those who study and research head and brain injuries that helmets may protect the scalp and skull from injury, and may increase the distance of deceleration, but cannot directly prevent harmful brain motion and deformation within the intracranial cavity. In one embodiment, a collision warning and impending impact sensor which uses lidar and ultrasound detectors are incorporated into a helmet worn by the user. Accelerometers and gyroscopic based fall detectors and algorithms are also incorporated into the helmet, and detect the falling event (Huynh 2015). The combination of data from these detectors is analyzed by the CPU which enables proper timing of deployment of the compression device. The compression device prevents or reduces abnormal and harmful brain motion upon impact, thus greatly augmenting the total head and brain protective capability afforded by the helmet alone, and preventing or reducing the degree of traumatic brain injury or concussion.

Example 6

Elderly persons who may have an increased propensity towards falling can be at increased risk of brain injuries. For example, the elderly individual may be more prone to suffering acute and chronic subdural hematomas due to brain atrophy which can stretch the bridging cerebral veins rendering them more likely to rupture when the brain moves abnormally due to a fall. Prevention or reduction of abnormal brain movement by displacing cerebrospinal fluid towards the intracranial compartment and stiffening the brain by reducing compliance in users with brain atrophy represents an effective means to reduce this type of brain injury. For this type of user, a helmet may not be practical or acceptable and fall sensing devices worn on the torso or incorporated into a pants belt or a vest garment which detects falls can be an excellent solution.

Example 7

Individuals who engage in boxing, martial arts, and related sport combat activities are at significant risk for head and brain injuries from impacts and abnormal, harmful internal brain rotation and deformation. The inflating bag component of the compression device that may be most suitable for users engaging in sports where blows to the torso are common can be constructed from a very thin elastomeric polymer utilizing nylon, which is a material commonly used for vehicular airbags. The deflated nylon sac can be collapsed into a waistband anteriorly and the compressed gas container can be positioned and padded for protection in the waistband posteriorly, where it is less likely to be damaged by a blow. The sensing array and CPU could be incorporated into a mouthguard which communicates wirelessly with the compressed gas container, since the blow to the head incurred during combat sports most likely would come from a forward facing position. A prolonged inflation duration is enabled by incorporation of a gas release valve which releases gas very slowly, over several minutes or less, which can afford increased brain protection in the event of a rapidly occurring series of blows.

Example 8

Another of the various embodiments may utilize sensors that indicate position, movement, trajectory, and proximity that are worn by a secondary user or incorporated in an object not always associated with the primary user. The event leading to a blow, impact, or collision which can harm the primary user is detected by a sensing array worn by the secondary user, for example an opposing sports opponent, for example as in the game of American football, or incorporated in a separate object such as a soccer ball whose trajectory is to be changed by deliberate use of a soccer player's head, and is designed and programmed to activate the compression device worn by the primary user.

Example 9

Another of the various embodiments may pertain to mitigation of brain injury from blasts, such as can occur in the military and combat setting. Blasts from bomb explosions can produce a high pressure wave, followed by a zone of low pressure. Research has shown that intracranial pressure can be elevated initially, and possibly followed by a cavitation process in brain tissue. Some evidence suggests that the types of brain injuries due to blasts may have different neuropathological characteristics compared to impact injuries, such as astroglial scarring and evidence of tissue and cell injuries at brain tissue interfaces. Sensing of a blast wave such as by a pressure sensing device mounted on a vehicle containing the user, or mounted on a object remote from the user, can allow for wireless signaling and triggering of protection just prior to arrival of the blast wave. In this case, activation of the protective device can transiently reduce the intracranial pressure of the user, by decompressing the abdomen/pelvis, rapidly followed by a device induced increase in intracranial pressure, to protect the brain from the low pressure zone and/or secondary head and brain impact which commonly occurs from blast injuries, due to impacts from flying objects or from the user impacting objects, or impacting the inside of a vehicle, which commonly occurs in improvised explosive device events affecting occupants of military vehicles.

The need for and benefits of intracranial pressure reduction, and optimization of timing, degree, and duration of pressure reduction in the event of blast events is determined by in vitro, in vivo, preclinical, clinical testing, as well as using simulations, and models of blast events, and imaging of brain motion and deformation, and cerebrospinal fluid motion and movement. Testing that aids in device optimization can also include intracranial pressure measurements in vivo, and various types of simulations known in the art. Likewise, the combination of, and optimal timing, duration, and degree of intracranial pressure reduction and increase in venous return, followed by transient intracranial pressure increase and venous return reduction is modeled, simulated, and tested, to optimize device design and function. In a similar manner, the surface area of the abdomen and optionally the pelvis that the suction device interfaces with, and the shape, dimensions, configuration, and height of the suction device dome, as well as the construction materials of the suction device are optimized by way of in vitro, in vivo testing, simulations and modeling, and preclinical, clinical testing, and imaging.

Various embodiments have been described herein for exemplary illustration. Modifications of the various embodiments described herein could be made by those skilled in the art. All such modifications, which are within the scope of the claims, are intended to be inclusive within the scope and spirit of the one or more of the various embodiments.

Example 10

At least one external ultrasound transducer and/or at least one photoacoustic device is positioned such that at least one ultrasound beam or beamlet can converge on a known target within the CSF axis, or onto a venous compartment capable of creating a very rapid, transient protective rise in intracranial CSF pressure, just prior to anticipated harmful head motion and brain impact or deformation.

Definitions

The user is defined as an individual who is human or animal, who utilizes the brain protection apparatus.

The term sensing devices and sensing device array encompasses at least one of, and any combination of a pressure sensor, and/or accelerometer, and/or gyroscope, and/or ultrasound, infrared, electromagnetic, laser, machine vision/imaging apparatus, radar, lidar, and related devices.

The term compression device encompasses at least one apparatus capable of exerting force against the abdomen, and/or pelvis, and/or thorax, in an anterior location or an anterolateral location.

The term brain and brain tissue includes neurons, axons, astrocytes, other brain cells, blood vessels and vascular structures within the brain, and the brain stem.

The term cerebrospinal fluid refers to the fluid surrounding the brain and within the brain parenchyma, including the cerebral ventricular system.

The term body wall can refer to the thorax, abdomen, pelvis, individually, or in any combination.

EXAMPLES FOR OTHER VARIOUS EMBODIMENTS

Example 1

Photoacoustic energy is applied in a discrete zone and depth to the vagal nerve stimulation points in the ear, in particular to the auricular branch of the vagus nerve, and/or to the cervical (neck) branch of the vagus nerve, and/or along the length of the vagus nerve.

A variety of disorders have been investigated and may be treated using noninvasive vagal nerve stimulation, including headaches, tinnitus, depression, epilepsy, various pain disorders, disturbances involving cardiac regulation, mental disorders including schizophrenia. Post-infectious adverse sequelae can be treated by the combination of light directed at the target tissue site, augmented in an additive or synergistic fashion by the combined effect of light and ultrasound at the treatment site.

The external, noninvasive device utilizes both focused light and focused ultrasound, enabling a large number of vagal nerve stimulation parameters to be easily, safely, and conveniently set, altered as needed, and monitored. The use of ultrasound imaging incorporated to the function of the device enables precise aiming of the device energy, comprising light and ultrasound, at the target, due to the imaging capability, as well.

Vagal nerve stimulation parameters to be optimized experimentally include polarity, stimulation frequency, duration, pulse width, intensity, waveform, and duty cycle.

Preferred targets in the ear include vagal nerve branches within the cavum conchae, the cymbae conchae, the tragus, and the antihelix. The preferred targets in the neck include the lesser occipital nerve, the great auricular nerve, the accessory nerves, the supraclavicular nerves, and transverse cervical nerves. It is understood that any combination of nerves, or individual nerves, unilaterally, or bilaterally (one or both ears, one or both sides of the neck) can be stimulated.

Example 2

Any number of known acupuncture points can be stimulated, in a discrete zone, and depth by the device, which utilizes the combination of localized ultrasound pulses and targeted light, which may be pulsed, to stimulate the desired acupuncture point(s). In addition, neural tissues may be directly stimulated in a targeted manner, to increase or decrease neural activity, which can reduce pain, stimulate muscle contraction, increase or decrease neuronal function, as examples, which in no manner preclude other uses.

Example 3

A series of experiments are performed utilizing a tubular, hollow polymeric phantom which is intended to simulate the oral cavity, the nasopharynx, and the upper and lower respiratory tract. Water vapor is generated using a steam generator capable of expressing water droplets of varying sizes to ascertain the droplet size ranges which afford the furthest red light penetration into the depths of the phantom.

Example 4

Water vapor is inhaled through a circular or oblong mouthpiece tube, similar to that incorporated into inhaler devices used for asthma treatment, or similar to that used for nebulized mist treatments. A light source, preferably comprised of one or more red LEDs, is incorporated into the mouthpiece tube, with light directed into the water vapor droplet stream, enabling light to be delivered into the oral cavity, the nasopharynx, and the upper and lower respiratory tract. The red light reduces tissue inflammation, promotes tissue healing, and can also activate red light absorbing photosensitizers administered locally or systemically. Alternatively, the tube transmitting water vapor is connected to a facemask, fitting comfortably over the mouth and nose, which enables light from a light source incorporated into the mask to be aimed and launched into the upper and lower respiratory tract.

Example 5

The photoacoustic effect enable ultrasound mediated imaging, which aids in real-time visualization of photodynamic therapy, which is of great value in the treatment of cancerous deposits, since the photoacoustic parameters can be adjusted to maximize the desired effect. For example, the use of a photoacoustic technique to induce the ischemia reperfusion can be monitored in real-time during the therapy session, to ascertain adequate cessation of blood flow with subsequent reflow. By not requiring complete and permanent vascular closure, the need for high energy delivery is avoided, safety is increased, and deleterious and painful inflammation is avoided, which can be tumor promoting conditions.

Example 6

The photoacoustic effect is utilized to provide combined light therapy and ultrasound to the left and/or right stellate ganglion, in the cervical area, which has been shown to reduce autonomic dysfunction leading to cardiac arrhythmias. The intensity of light therapy . . . .

Example 7

The photoacoustic effect is used to treat a cancerous deposit, by aiming and directing the light source, which may be emitted from one or more photoacoustic devices, after administration of one or more photosensitizers, systemically or by way of local application. The antitumor effect induced by the acoustic pulse and by the directed light is monitored in real-time by an incorporated ultrasound transducer, which is used to alter the therapy to increase efficacy if required. For example, after a fixed amount of one or more photosensitizers is administered, the ultrasound transducer is used to image the cancerous deposit to ascertain change in image signal and reduction in blood flow, indicative of a beneficial anticancer effect. If no changes occur, the light intensity is increased, to improve the photodynamic and sonodynamic effect.

Example 8

A variety of light delivery intensity and pulse parameters and modes, wavelengths, and wavebands, photoacoustic stimulation parameters, treatment time lengths, treatment schedules, and the like can be assessed and analyzed using ascending dose intensity study designs, and appropriate statistical analysis to ascertain effective treatment parameters, which also informs optimized light device design and engineering.

Example 9

A patient suffering from post-infectious sequelae of viral and microbial infection, which can include difficulty with memory, concentration, and mental executive function, cardiac and pulmonary problems, autonomic instability, pain, headaches, reduced exercise tolerance, fevers, flu-like symptoms and fatigue, autoimmune phenomenon and the like, is treated using the photoacoustic device which stimulates the vagus nerve, and which can be directed to other tissues to stimulate or decrease function. The general treatment parameters are determined by way of preclinical research and clinical trials, using well known research methods. Treatments may be individualized by adjusting the intensity and duration of the photoacoustic effect, in real-time, for in sequence, after determination of general treatment parameters.

Effects can be measured by capturing data relating to inflammatory blood markers, physiologic parameters such as heart rate variability, quality of life measurements, pain scales, disability scores and the like, which can be analyzed and used to optimize the therapy sessions.

Example 10

A hollow organ such as the lung is illuminated externally by a light source array, such as a focused LED array aiming light from a location on the surface of the thorax, which generates a photoacoustic ultrasonic pulse wave within the lung tissue. This technique enables delivery of an ultrasonic pulses, which are therapeutic as a single modality, or which may be used to sonodynamically activate one or more photosensitizers, in a manner not feasible using external ultrasound which does not transmit well through air filled organs and spaces.

Additionally, in one or more of the various embodiments or examples, artificial intelligence (AI) feedback and/or heart rate variability (HRV) feedback may be provided before, during, after, wireless communication to external devices.

What is claimed as new and desired to be protected by Letters Patent of the United States is:

1. A method, comprising:
- applying one or more photosensitizers to target tissue;
- employing one or more light devices to direct one or more pulsed light beams at the target tissue, wherein the one or more pulsed light beams cause generation of one or more acoustic waves in the target tissue;
- selecting one or more wavelengths for the one or more pulsed light beams to cause photoactivation of the one or more photosensitizers at the target tissue and minimize absorption of the one or more pulsed light beams by non-target tissue;
- employing the more pulsed light beams to generate one or more selected frequencies of the one or more acoustic waves that cause sonodynamic activation of the one or more photosensitizers at the target tissue; and
- combining the photoactivation and the sonodynamic activation of the one or more photosensitizers to cause generation of singlet oxygen at the target tissue and promote an increase in healing and a reduction of inflammation and pain at the target tissue.

2. The method of claim 1, further comprising:
- employing the one or more acoustic waves to cause the sonodynamic activation of the one or more photosensitizers on a surface of the object.

3. The method of claim 1, wherein applying the one or more photosensitizers further comprises:
- employing the one or more acoustic waves to cause the sonodynamic activation of the one or more photosensitizers within the object.

4. The method of claim 1, further comprising:
- employing modification of one or more of the wavelength, an intensity, or a frequency of the one or more pulsed light beams to adjust a rate of the photoactivation of the one or more photosensitizers.

5. The method of claim 1, further comprising:
- employing modification of one or more of an intensity or a frequency of the one or more pulsed light beams to adjust the sonodynamic activation of the one or more photosensitizers.

6. The method of claim 1, further comprising:
- employing a plurality of different wavelengths for the pulsed light beams to generate a plurality of different depths of penetration within the target tissue by the one or more pulsed light beams and the one or more acoustic waves.

7. The method of claim 1, wherein the one or more light beams further comprise one or more non-ionized light beams.

8. The method of claim 1, further comprising:
employing the one or more acoustic waves to generate ultrasound stimulation within the object target tissue.

9. The method of claim 1, further comprising:
employing the one or more acoustic waves to generate one or more ultrasound visualizations of an interior of the target tissue.

10. The method of claim 1, wherein the one or more pulsed light beams, further comprise:
employing a plurality of wavelengths that range from 800 nanometers to 2,500 nanometers; and
employing a plurality of frequencies that range from one to ten mega hertz (MHz).

11. An apparatus, comprising:
one or more light devices to direct one or more pulsed light beams at target tissue that includes one or more photosensitizers, wherein the one or more pulsed light beams cause generation of one or more acoustic waves in the target tissue; and
a processor that performs actions, including:
selecting one or more wavelengths for the one or more pulsed light beams to cause photoactivation of the one or more photosensitizers and minimize absorption of the one or more pulsed light beams by non-target tissue;
employing the more pulsed light beams to generate one or more selected frequencies of the one or more acoustic waves that cause sonodynamic activation of the one or more photosensitizers; and
combining the photoactivation and the sonodynamic activation of the one or more photosensitizers to cause generation of singlet oxygen at the target tissue and promote an increase in healing and a reduction of inflammation and pain at the target tissue.

12. The apparatus of claim 11, further comprising:
employing the one or more acoustic waves to cause the sonodynamic activation of the one or more photosensitizers on a surface of the target tissue.

13. The apparatus of claim 11, wherein applying the one or more photosensitizers further comprises:
employing the one or more acoustic waves to cause sonodynamic activation of the one or more photosensitizers within the target tissue.

14. The apparatus of claim 11, further comprising:
employing modification of one or more of the wavelength, an intensity or a frequency of the one or more pulsed light beams to adjust a rate of photoactivation of the one or more photosensitizers.

15. The apparatus of claim 11, further comprising:
employing modification of one or more of an intensity or a frequency of the one or more pulsed light beams to adjust the sonodynamic activation of the one or more photosensitizers caused by the one or more acoustic waves.

16. The apparatus of claim 11, further comprising:
employing a plurality of different wavelengths for the pulsed light beams to generate a plurality of different depths of penetration within the target tissue by the one or more pulsed light beams and the one or more acoustic waves.

17. The apparatus of claim 11, wherein the one or more light beams further comprise one or more non-ionized light beams.

18. The apparatus of claim 11, further comprising:
employing the one or more acoustic waves to generate ultrasound stimulation within the target tissue.

19. The apparatus of claim 11, further comprising:
employing the one or more acoustic waves to generate one or more ultrasound visualizations of an interior of the target tissue.

20. The apparatus of claim 11, wherein the one or more pulsed light beams, further comprise:
employing a plurality of wavelengths that range from 800 nanometers to 2,500 nanometers; and
employing a plurality of frequencies that range from one to ten mega hertz (MHz).

* * * * *